(12) United States Patent
Wang et al.

(10) Patent No.: US 12,733,834 B2
(45) Date of Patent: Sep. 15, 2026

(54) METHODS, APPARATUSES AND ELECTRONIC DEVICES FOR MAGNETIC RESONANCE IMAGING SCANNING

(71) Applicant: Anhui Huami Information Technology Co., Ltd., Hefei (CN)

(72) Inventors: Kongqiao Wang, Hefei (CN); Li Guo, Hefei (CN); Mingxi Zhao, Hefei (CN)

(73) Assignee: Anhui Huami Information Technology Co., Ltd., Hefei (CN)

(*) Notice: Subject to any disclaimer, the term of this patent is extended or adjusted under 35 U.S.C. 154(b) by 262 days.

(21) Appl. No.: 18/413,257

(22) Filed: Jan. 16, 2024

(65) Prior Publication Data

US 2024/0148268 A1 May 9, 2024

Related U.S. Application Data

(63) Continuation of application No. PCT/CN2022/091295, filed on May 6, 2022.

(30) Foreign Application Priority Data

Aug. 12, 2021 (CN) ........................ 202110926206.7

(51) Int. Cl.

| | |
|---|---|
| ***A61B 5/05*** | (2021.01) |
| ***A61B 5/055*** | (2006.01) |
| ***G06T 3/40*** | (2006.01) |
| ***G06V 10/44*** | (2022.01) |
| ***G06V 10/74*** | (2022.01) |

(52) U.S. Cl.

CPC ................ *A61B 5/055* (2013.01); *G06T 3/40* (2013.01); *G06V 10/44* (2022.01); *G06V 10/761* (2022.01)

(58) Field of Classification Search

CPC ...... A61B 5/055; G06V 10/44; G06V 10/761; G06T 3/40

See application file for complete search history.

(56) References Cited

U.S. PATENT DOCUMENTS

| | | | |
|---|---|---|---|
| 5,089,889 | A | 2/1992 | Sugiyama |
| 2005/0001618 | A1 | 1/2005 | Bydder |

(Continued)

FOREIGN PATENT DOCUMENTS

| | | | |
|---|---|---|---|
| CN | 102018514 | A | 4/2011 |
| CN | 104181485 | A | 12/2014 |

(Continued)

OTHER PUBLICATIONS

International Search Report and English Translation for International Application No. PCT/CN2022/091295 dated Jun. 29, 2022.

*Primary Examiner* — Joel F Brutus

(74) *Attorney, Agent, or Firm* — Young Basile Hanlon & MacFarlane, P.C

(57) ABSTRACT

Methods, apparatuses, electronic devices for MRI scanning are provided, in which in each scanning plane segment, original k-space data of a current scanning plane is obtained, and a first plane image of the current scanning plane is generated based on the original k-space data, the type of the current scanning plane is determined, and the second plane image of the current scanning plane is generated based on the first plane image of the current scanning plane with a prediction mode corresponding to the type of the current scanning plane.

20 Claims, 8 Drawing Sheets

(56) References Cited

U.S. PATENT DOCUMENTS

| | | | | |
|---|---|---|---|---|
| 2009/0161933 | A1 | 6/2009 | Chen | |
| 2014/0376794 | A1* | 12/2014 | Dumoulin | G01R 33/5611 382/131 |
| 2018/0285695 | A1 | 10/2018 | Guo et al. | |
| 2019/0361079 | A1 | 11/2019 | Takeshima | |
| 2020/0225308 | A1 | 7/2020 | Dosenbach et al. | |
| 2020/0341091 | A1 | 10/2020 | Zheng et al. | |
| 2021/0174939 | A1 | 6/2021 | Huang et al. | |

FOREIGN PATENT DOCUMENTS

| | | | |
|---|---|---|---|
| CN | 104434108 | A | 3/2015 |
| CN | 109076237 | A | 12/2018 |
| CN | 112526423 | A | 3/2021 |
| CN | 112649775 | A | 4/2021 |
| CN | 112995669 | A | 6/2021 |

* cited by examiner

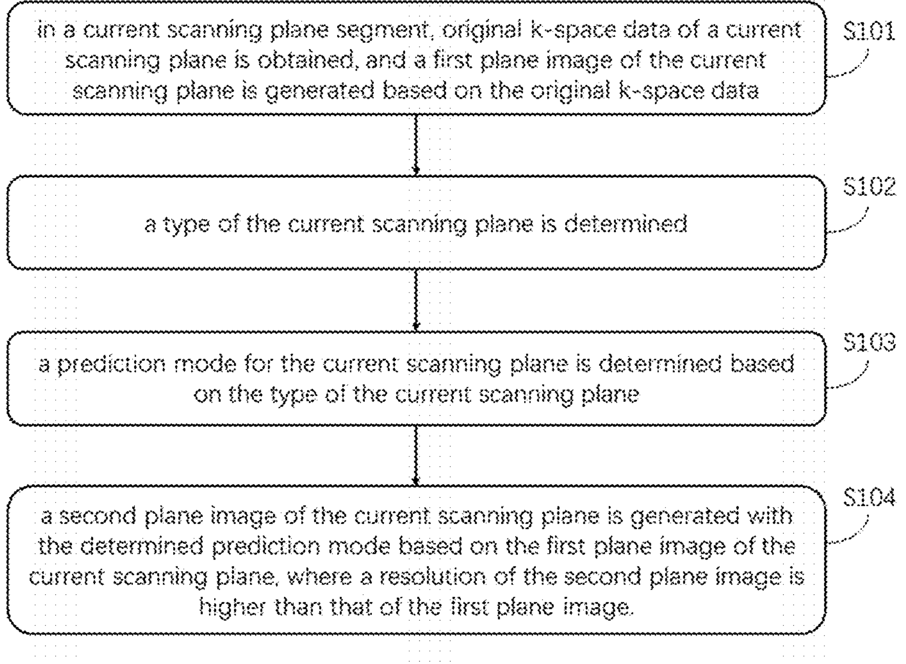
FIG. 1
in a case where the current scanning plane is of the first type, MR intra-frame imaging is performed for the current scanning plane based on the first plane image of the current scanning plane, and the second plane image of the current scanning plane is generated
S201
FIG. 2
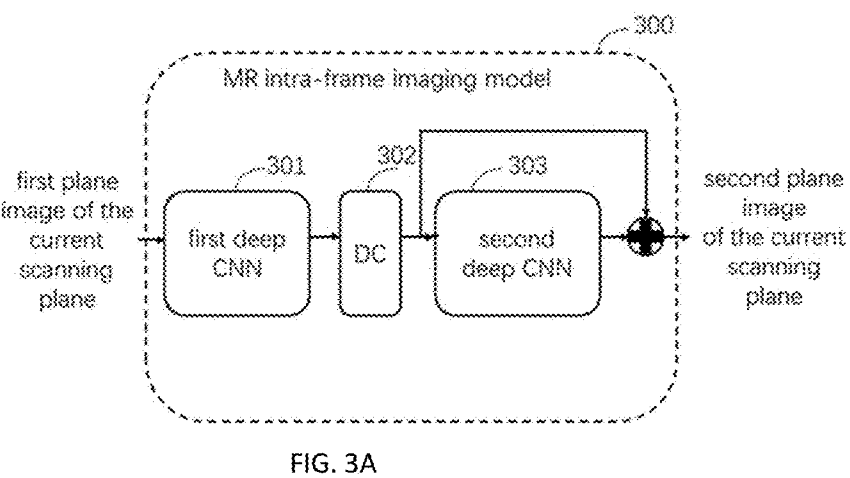
FIG. 3A in the case that the structural similarity is less than or equal to the preset similarity threshold, move the current scanning plane to the next scanning plane segment

Figures 7, 8, 9:
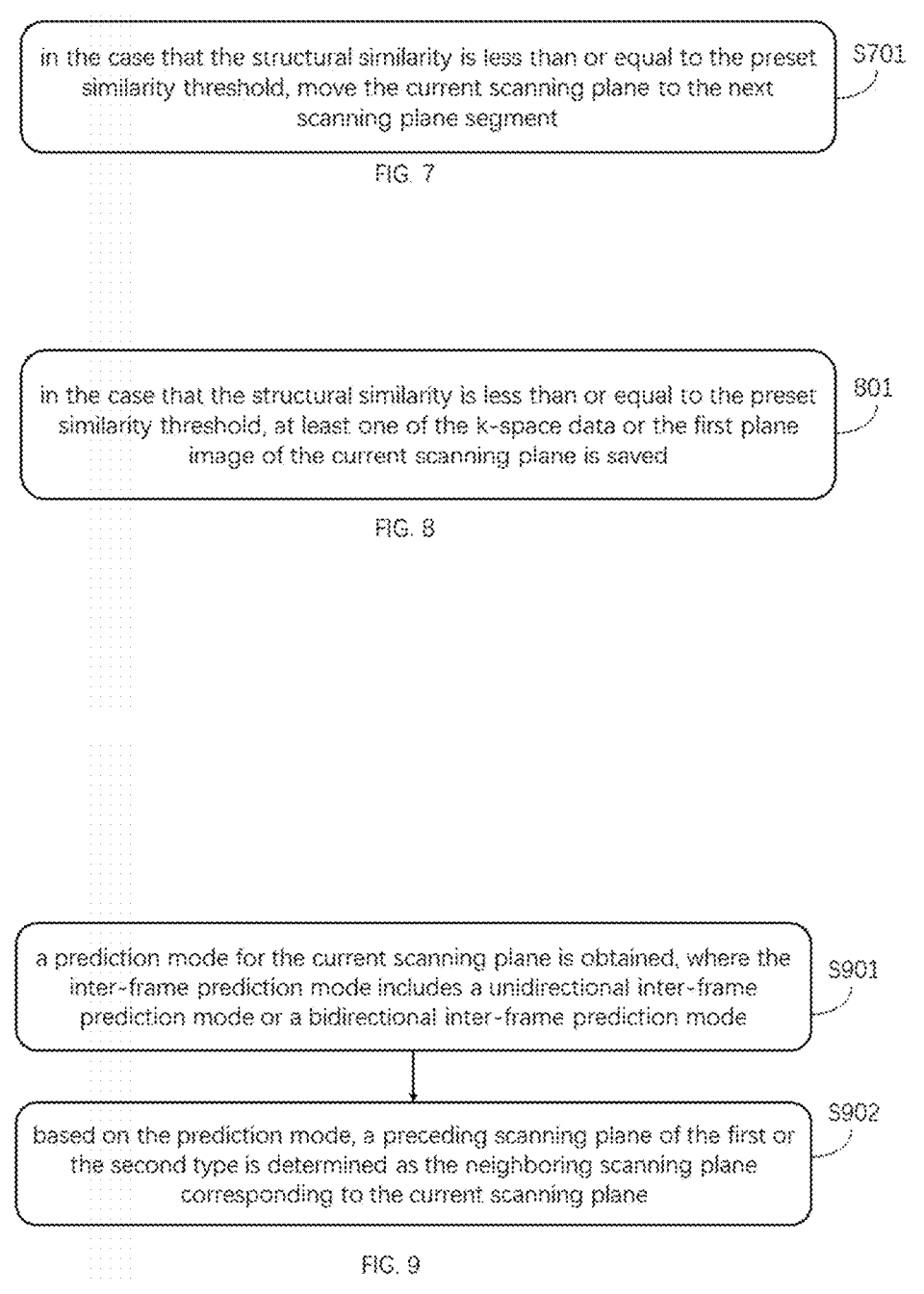

S701

FIG. 7 in the case that the structural similarity is less than or equal to the preset similarity threshold, at least one of the k-space data or the first plane image of the current scanning plane is saved

801

FIG. 8 a prediction mode for the current scanning plane is obtained, where the inter-frame prediction mode includes a unidirectional inter-frame prediction mode or a bidirectional inter-frame prediction mode

S901 based on the prediction mode, a preceding scanning plane of the first or the second type is determined as the neighboring scanning plane corresponding to the current scanning plane

S902

FIG. 9 in the case where the current scanning plane is a plane set including a plurality of sub-scanning planes, starting from the initial sub-scanning plane in the plane set, an MR inter-frame prediction is performed for each sub-scanning plane in the plane set to generate a second plane image corresponding to the sub-scanning plane. This process continues until imaging of all the sub-scanning planes in the plane set is completed, and the method proceeds to the next scanning plane or the next scanning plane segment

Figures 12, 13:
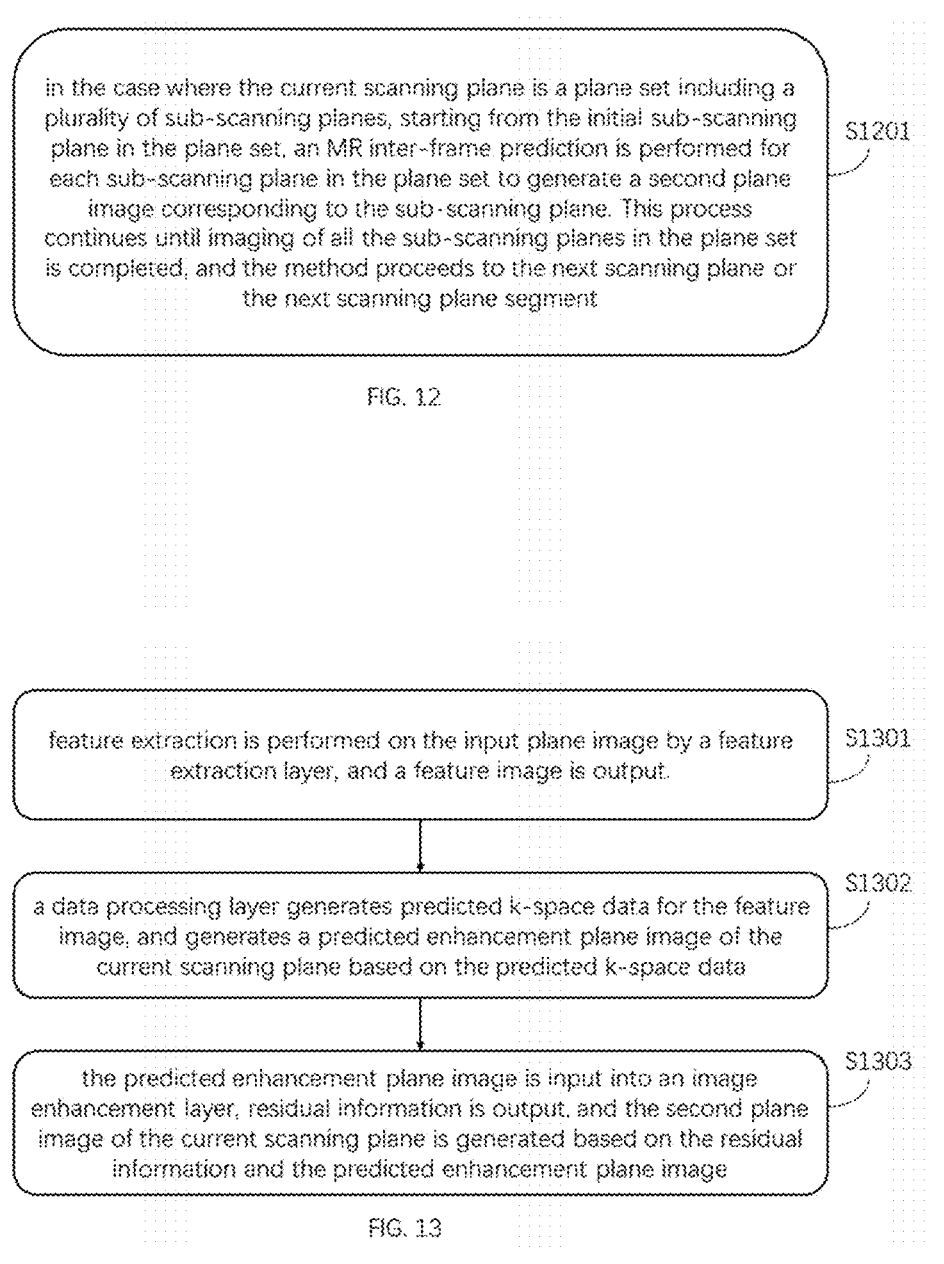

S1201

FIG. 12 feature extraction is performed on the input plane image by a feature extraction layer, and a feature image is output.

S1301 a data processing layer generates predicted k-space data for the feature image, and generates a predicted enhancement plane image of the current scanning plane based on the predicted k-space data

S1302 the predicted enhancement plane image is input into an image enhancement layer, residual information is output, and the second plane image of the current scanning plane is generated based on the residual information and the predicted enhancement plane image

METHODS, APPARATUSES AND ELECTRONIC DEVICES FOR MAGNETIC RESONANCE IMAGING SCANNING

CROSS-REFERENCE TO RELATED APPLICATION(S)

The present application is a continuation of PCT/CN2022/091295, filed on May 6, 2022, which claims priority and benefit to Chinese Patent Application No. 202110926206.7, filed on Aug. 12, 2021, the entire contents of both of which are hereby incorporated by reference.

TECHNICAL FIELD

The present disclosure relates the field of magnetic resonance imaging technologies, and more specifically, to a method, apparatus, electronic device, computer readable storage medium, computer program product, and computer program for MRI scanning.

BACKGROUND

Magnetic Resonance Imaging (MRI), as an advanced diagnostic tool in radiology, has begun to be integrated with surgical robots to perform complex surgical procedures, such as deep brain tumor ablation surgeries and the like. Therefore, there is a need for high quality imaging and high imaging speed for MRI.

In the related technologies, the scan time for each slice of MRI images has been significantly reduced, greatly improving the speed of MRI imaging. However, the reduction in scan time can have an impact on the image quality of each obtained MRI slice, and a negative correlation between scan time and image quality is presented. Therefore, how to achieve high-speed and high-quality MRI imaging is currently an urgent issue to be solved.

SUMMARY

The present application is intended to address, at least in part, one of the technical problems in the above-described technologies.

To achieve the above objectives, a first aspect of this application provides a method for MRI scanning. The method includes: acquiring original k-space data of a current scanning plane in a current scanning plane segment, and generating a first plane image of the current scanning plane based on the original k-space data; determining a type of the current scanning plane; determining a prediction mode for the current scanning plane based on the type of the current scanning plane, wherein the prediction mode comprises a MR intra-frame imaging mode or a MR inter-frame prediction mode; and generating a second plane image of the current scanning plane with the determined prediction mode based on the first plane image of the current scanning plane, wherein a resolution of the second plane image is greater than a resolution of the first plane image.

In some implementations, it is determined whether the current scanning plane is of a first type. In response to the current scanning plane not being of the first type, a neighboring scanning plane corresponding to the current scanning plane is determined, and imaging prediction is performed for the current scanning plane based on the first plane image of the current scanning plane and the second plane image of the neighboring scanning plane to generate the second plane image of the current scanning plane.

A second aspect of the present application provides an apparatus for MRI scanning performing the method provided in the first aspect.

A third aspect of the application provides an electronic device, including: at least one processor; and a memory communicatively connected to the at least one processor; where the memory stores instructions executable by the at least one processor, and execution of the instructions by the at least one processor causes the at least one processor to perform the above method provided in the first aspect.

A fourth aspect of the application provides non-transitory computer readable storage medium storing computer instructions, where the computer instructions are configured to cause a computer to execute the above method provided in the first aspect.

A fifth aspect of the application provides a computer program product including a computer program, where the computer program, when executed by a processor, implements the method provided in the first aspect.

The method and apparatus for MRI scanning provided in the disclosure obtains the original k-space data for the current scanning plane of each scanning plane segment, generates the first plane image corresponding to the current scanning plane, and then determines the type the current scanning plane. The second plane image corresponding to the current scanning plane is generated based on the first plane image with a prediction mode corresponding to the type of the current scanning plane. In the present disclosure, the low-resolution first plane image is first obtained for each scanning plane and then processed to obtain the high-resolution second plane image, effectively shortening the imaging time, and reducing the scanning time. Separate scanning imaging is performed for different scanning planes in each scanning plane segment, ensuring image quality, and achieving the goal of high-speed, high-quality scanning and imaging for MRI.

BRIEF DESCRIPTION OF THE DRAWINGS

The foregoing and/or additional aspects and advantages of the present disclosure will become apparent and easily understood from the following description of the implementations in conjunction with the accompanying drawings.

FIG. 1 is a schematic flowchart illustrating a method for MRI scanning in an implementation of the present disclosure.

FIG. 2 is a schematic flowchart illustrating the method for MRI scanning in another implementation of the present disclosure.

FIG. 3A is a schematic flowchart illustrating an MR intra-frame imaging model in an implementation of the present disclosure.

FIG. 7 is a schematic flowchart illustrating the method for MRI scanning in another implementation of the present disclosure.

FIG. 8 is a schematic flowchart illustrating the method for MRI scanning in another implementation of the present disclosure.

FIG. 9 is a schematic flowchart illustrating the method for MRI scanning in another implementation of the present disclosure.

FIG. 12 is a schematic flowchart illustrating the method for MRI scanning in another implementation of the present disclosure.

FIG. 13 is a schematic flowchart illustrating the method for MRI scanning in another implementation of the present disclosure.

DETAILED DESCRIPTION

Figures 3B, 4:
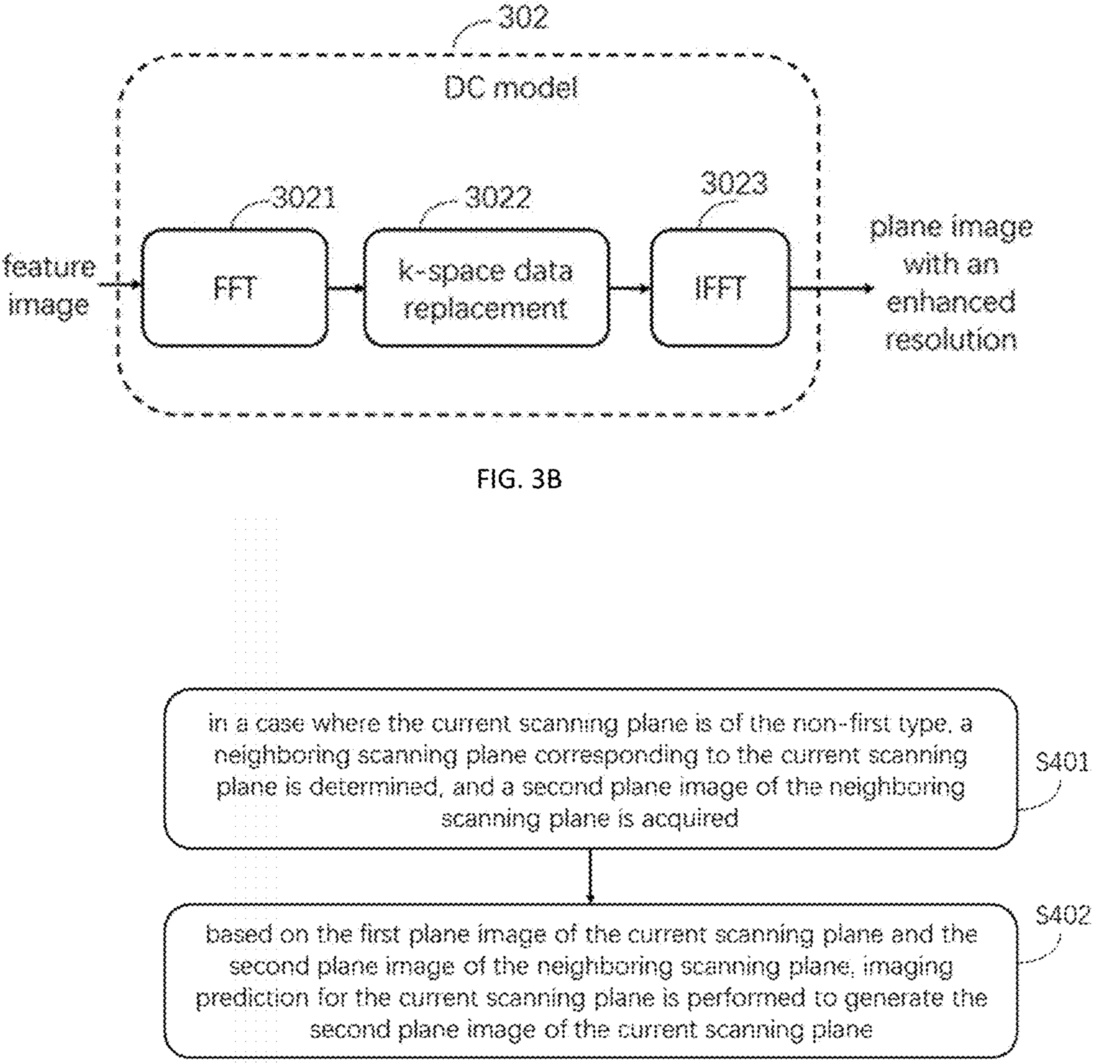
FIG. 3B is a schematic flowchart illustrating an example DC model in the MR intra-frame imaging model in an implementation of the present disclosure.
FIG. 4 is a schematic flowchart illustrating data processing of a DC calculation architecture model in an implementation of the present disclosure.

Implementations of the present disclosure are described in detail below. Examples of the implementations are illustrated in the accompanying drawings, where a same or similar labeling throughout the description denotes a same element, similar elements or elements having a same or similar functions. The implementations described below with reference to the accompanying drawings are just examples. They are intended to be used in explaining the present disclosure and are not to be construed as a limitation of the present disclosure.

The methods, apparatuses, electronic devices, and computer-readable storage medium for magnetic resonance imaging (MRI) scanning presented in implementations of the present disclosure are described below in conjunction with the accompanying drawings.

FIG. 1 shows a flowchart of the method for MRI scanning in an implementation of the present disclosure. As shown in FIG. 1, the method includes S101-S104.

At S101, in a current scanning plane segment, original k-space data of a current scanning plane is obtained, and a first plane image of the current scanning plane is generated based on the original k-space data.

Nuclear Magnetic Resonance Imaging (NMRI), also known as spin imaging or Magnetic Resonance Imaging (MRI), utilizes nuclear magnetic resonance (NMR) technologies. Based on the different attenuation of released energy in different structures of a substance, and detected electromagnetic waves emitted by an applied gradient magnetic field, the location and type of nuclei that make up the object can be determined, and accordingly, a structural image of the interior of the object can be plotted.

In general, MRI is commonly used in medicine for the examination and imaging of the tissue structure of a human body. Within the human body, there is a widespread presence of atomic nuclei containing singular protons, such as hydrogen nuclei, which exhibits spin motions. By placing these spinning protons in a strong external magnetic field, they align in two directions either parallel or antiparallel to the external magnetic field. In this scenario, a radiofrequency (RF) pulse of a specific frequency is used to excite these atomic nuclei with single protons, causing the nuclei to resonate by absorbing a certain amount of energy, i.e., the magnetic resonance phenomenon. In practice, after the RF pulse emission is stopped, the atomic nuclei with single protons that resonance gradually release the absorbed energy. Consequently, their phase and energy levels return to the state before being excited by the RF pulse. This process is referred to as the relaxation process, and the length of time spent in the relaxation process is known as the relaxation time.

Different tissue structures of the human body require different relaxation times, and the difference in relaxation times between different tissue structures forms the basis of magnetic resonance imaging. Typically, during a magnetic resonance examination, the tissue structures of the human body to be examined are divided into a plurality of inspection planes. By imaging each inspection plane separately, a complete image of the tissue structure to be detected is then generated.

In the present disclosure, at least one scanning plane scanned during a specific time period can be treated as a scanning plane segment, and the at least one scanning plane included in the scanning plane segment can be obtained by scanning the same body part or the same region of a body part. The at least one scanning plane included in the scanning plane segment can be arranged in sequence according to scanning parameters, a scanning order, corresponding spatial positions, or the like, which is not limited herein.

During the MRI scanning and imaging process, for each scanning plane, the acquired image data is stored in k-space, and the original k-space data corresponding to each scanning plane can be obtained from k-space. The original k-space data contains partial image data for the current scanning plane, which is used to generate the first plane image for the current scanning plane.

In the implementations, different sampling rates are applicable to different parts of the tissue structures of the human body. During the MRI scanning and imaging process, it is necessary to adjust the sampling rate promptly for each scanning plane to obtain image data with high accuracy. In some implementations, under-sampling is used to collect image data for the current scanning plane, and the scanning frequencies for the current scanning plane can be adjusted in real-time based on the actual situation to obtain precise image data for the current scanning plane, which is then stored in k-space.

Furthermore, a designated image data processing method, such as inverse Fourier transform (IFFT) and/or the like, can be used to transform the original k-space data into a plane image.

At S102, a type of the current scanning plane is determined.

The type of the current scanning plane may include a first type or a non-first type. The non-first type may include one or more types. The first type and the non-first type correspond to different under-sampling factors. In some implementations, the first type of scanning plane corresponds to a first under-sampling factor smaller than an under-sampling factor corresponding to the non-first type of scanning plane.

In the present disclosure, the k-space data may be obtained by under-sampling, and the scanning for MRI can be carried out with at least two under-sampling factors, i.e., at least two sampling rates, thereby forming at least two types of scanning planes, referred to as the first type of scanning plane and the non-first type of scanning plane, where the non-first type of scanning plane may include at least one type of scanning plane. The k-space data of the first type of scanning plane may be obtained by scanning with the first under-sampling factor, and the k-space data of the non-first type of scanning plane may be obtained by scanning with an under-sampling factor greater than the first under-sampling factor.

The scanning plane segment may include one or more of each type of scanning plane, and the number of different types of scanning planes in the scanning plane segment can be the same or different. In some implementations, since a smaller under-sampling factor requires a longer scanning time, in order to improve scanning efficiency, comparing to a greater under-sampling factor among the at least two under-sampling factors, a smaller under-sampling factor may correspond to a smaller number of scanning planes in the scanning plane segment. In an example, the first under-sampling factor is the smallest among the at least two under-sampling factors, and there may be a smallest number of the first type of scanning plane in the current scanning plane segment. On the other hand, in order to ensure the imaging quality, the scanning plane segment can include at least one first type of scanning plane. In another example, the current scanning plane segment includes one first type of scanning plane and no non-first type of scanning plane. No limitation is set herein.

In some implementations, the at least two under-sampling factors include the first under-sampling factor and a second under-sampling factor, where the first under-sampling factor is smaller than the second under-sampling factor, and the second under-sampling factor corresponds to a second type of scanning plane included in the non-first type of scanning plane. The current scanning plane segment may include N first type of scanning planes and M second type of scanning planes, where N and M are integers equal to or greater than 1, and N and M may be the same or different. In some examples, in order to shortening the scanning time, N is less than M, but it is not limited herein.

In some implementations, the at least two under-sampling factors further include a third under-sampling factor, where the third under-sampling factor is smaller than the second under-sampling factor, and corresponds to a third type of scanning plane included in the non-first type of scanning plane. For instance, the at least two under-sampling factors include 4, 8 and 16. The at least two under-sampling factors may include other numbers of under-sampling factors, which is not limited in the present disclosure.

In some implementations, the scanning and imaging for the current scanning plane segment may begin with one or more first type of scanning planes, and then the non-first type of scanning planes are scanned and imaged. For example, in response to the scanning for MRI being started, scanning of a scanning plane I1 is carried out with the first under-sampling factor, so as to obtain the original k-space data of the first type of scanning plane I1, and subsequently, scanning of a scanning plane P1 is carried out with the second under-sampling factor, so as to obtain the original k-space data of the second type of scanning plane P1. In some implementations, if the at least two under-sampling factors further include the third under-sampling factor, the scanning of one or more third type of scanning planes may be carried out after the scanning of all the second type of scanning planes is completed, or the scanning of the second type of scanning planes are performed alternately with the scanning of the third type of scanning planes, which is not limited in the present disclosure.

In the scanning and imaging method for MRI disclosed in some implementations, the manner of generating the second plane image for the first type of scanning plane is different from that for the non-first type of scanning plane. Therefore, determination of the type of a particular scanning plane is required when scanning and imaging of the scanning plane is started.

In some implementations, it can be determined whether the current scanning plane is of the first type based on the position of the current scanning plane within its corresponding scanning plane segment. The scanning planes contained in each scanning plane segment are numbered according to the scanning order, and the number corresponding to the current scanning plane is obtained to determine the position of the current scanning plane within its corresponding scanning plane segment. For example, if the scanning planes within the scanning plane segment are numbered in the order of "1, 2, 3, 4, . . . ", and the sequential number of a scanning plane, which is 1, matches the initial number of the corresponding scanning plane segment, then the scanning plane is determined to be the first type of scanning plane, and a scanning plane with a sequential number other than 1 may be determined as the non-first type of scanning plane.

In some implementations, it can be determined whether the current scanning plane is of the first type based on whether a preceding scanning plane exists in the current scanning plane segment. If there is a preceding scanning plane for the current scanning plane in the current scanning plane segment, then the current scanning plane is determined to be the non-first type of scanning plane. If there is no preceding scanning plane for the current scanning plane in the current scanning plane segment, then the current scanning plane is determined to be the first type of scanning plane.

In some implementations, the under-sampling factor used for the current scanning plane may be recorded. the type of the current scanning plane is determined based on the recorded under-sampling factor and a correspondence between the under-sampling factors and the types of scanning planes. For example, if the scanning for MRI is performed with 4× under-sampling and 8× under-sampling, two types of scanning planes are included, where the scanning plane scanned with 4× under-sampling is of the first type, and the scanning plane scanned with 8× under-sampling is of the second type.

In some implementations, a scanning template can be determined, where the scanning template specifies which under-sampling factor is used for each of multiple times of scanning performed sequentially. In this case, the under-sampling factor corresponding to the current scanning plane as well as the type of the current scanning plane may be determined based on the order or position of the current scanning plane in the sequence of the current scanning plane segment and the scanning template. The specific implementations for determining the type of the current scanning plane are not limited in the present disclosure.

At S103, a prediction mode for the current scanning plane is determined based on the type of the current scanning plane, where the prediction mode includes an MR intra-frame imaging mode or an MR inter-frame prediction mode.

In some implementations, in response to the current scanning plane being of the first type, the MR intra-frame imaging mode is determined as the prediction mode for the current scanning plane.

In some implementations, in response to the current scanning plane being of the non-first type, the MR inter-frame prediction mode is determined as the prediction mode for the current scanning plane.

At S104, a second plane image of the current scanning plane is generated with the determined prediction mode based on the first plane image of the current scanning plane, where a resolution of the second plane image is higher than that of the first plane image.

The first type of scanning plane is scanned with the first under-sampling factor. The first under-sampling factor may be the minimum of the at least two under-sampling factors, or the first under-sampling factor is less than a specific value, such that the original k-space data contains more data of the first type of scanning plane, and the imaging of the first type of scanning plane can be performed with an intra-frame imaging mode. In the intra-frame imaging mode, the original k-space data of the first type of scanning plane is used to predict the unsampled part of the first type of scanning plane, so as to reconstruct a high-resolution plane image for the first type of scanning plane. Furthermore, the reconstructed high-resolution image of the first type of scanning plane may be used for imaging of one or more other types of scanning planes in the scanning plane segment.

In some implementations, the non-first type of scanning plane is scanned with an under-sampling factor greater than the first under-sampling factor. Since the k-space data of the non-first type of scanning plane contains fewer sampled data of the scanning plane, an inter-frame prediction mode can be used to reconstruct high-resolution images of non-first type of scanning planes. The inter-frame prediction mode may be a unidirectional inter-frame prediction mode or bidirectional inter-frame prediction mode, in which the reconstructed plane image of one or more other scanning planes as well as the k-space data of the current scanning plane are used to generate the high-resolution second plane image of the current scanning plane, thereby ensuring quality of the reconstructed plane images while improving scanning efficiency.

In some implementations, scanning and imaging of one or more first type of scanning planes is carried out, and the second plane images of the first type of scanning planes are obtained. Subsequently, one or more second type of scanning planes are sequentially scanned and imaged based at least in part on the second plane images of the first type of scanning planes, and thus obtaining the second plane images of the second type of scanning planes. In some implementations, based on the above, one or more third type of scanning planes are sequentially scanned and imaged based on at least in part on the second plane images of the first and/or second type of scanning planes, and so on. No limitation is set herein.

In some implementations, for the current scanning plane of the first type, the second plane image of the current scanning plane is generated based on the original k-space image data of the current scanning plane stored in the k-space. For instance, the first plane image is input into an image processing model for further resolution processing, so as to obtain the second plane image of the current scanning plane, thereby realizing high-quality imaging of the current scanning plane.

In some implementations, the image processing model can be a Magnetic Resonance (MR) intra-frame imaging model. For the first plane image of the first type of scanning plane in the current scanning plane segment, pixel information within the first plane image of the frame can be processed, resulting in high-resolution imaging corresponding to the first plane image of the frame. Furthermore, the model that processes the intra-frame pixel information of the first plane image of the first type of scanning plane to generate a high-quality image can be referred to as the MR intra-frame imaging model.

In some implementations, in a case where the current scanning plane is not of the first type, i.e., the current scanning plane is of the non-first type, a neighboring scanning plane corresponding to the current scanning plane is determined, and a second plane image of the neighboring scanning plane is acquired. Based on the first plane image of the current scanning plane and the second plane image of the neighboring scanning plane, imaging prediction for the current scanning plane is performed to generate the second plane image of the current scanning plane.

In some implementations, in the MR inter-frame prediction mode or the MR intra-frame imaging mode, the low-resolution first plane image of the current scanning plane, or the first plane image of the current scanning plane as well as one or more other inputs, such as the second plane image of the neighboring scanning plane, are input into an image processing model. The image processing model may include a feature extraction layer for feature extraction, such as a preset first deep convolutional neural network, to extract and process image features and output a feature image. The feature image is then input into a designated data processing layer, such as a network model with a Data Consistency (DC) architecture, for k-space data replacement. A plane image obtained after the replacement is then input into an image enhancement layer, such as a second deep convolutional neural network, for further processing, resulting in a high-resolution plane image, which is the second plane image corresponding to the first plane image of the current scanning plane.

Generally, magnetic resonance scanning and imaging can be used for examining the tissue structure of the human body. Any tissue structure of an individual can be divided into multiple scanning plane segments. By imaging each scanning plane segment and merging the images generated for each scanning plane segment, a complete image of the tissue structure can be obtained. Since multiple scanning planes are obtained based on division of a same tissue structure segmentation, there is a structural correlation between the scanning objects corresponding to each scanning plane segment, and further, each scanning plane within a scanning plane segment also has a structural correlation.

For the current scanning plane of the non-first type, based on the original k-space data of the current scanning plane, the first plane image of the current scanning plane can be obtained. Further, based on the second plane image of the neighboring scanning plane and the first plane image of the current scanning plane, the second plane image of the current scanning plane can be obtained.

In some implementations, an MR inter-frame prediction model can be used to process the first plane image of the current scanning plane and the second plane image of the neighboring scanning plane together, so as to obtain the second plane image of the current scanning plane.

It can be understood that, in the case that the current scanning plane is not of the first type, the pixel information in the first plane image of the current scanning plane and the pixel information in the second plane image of the neighboring scanning plane can be processed to generate the predicted second plane image corresponding to the first plane image of the current scanning plane. Furthermore, an image processing model which processes the pixel information in the first plane image of the non-first type of scanning plane and the pixel information in the second plane image of the neighboring scanning plane and generates a predicted high-quality image, is referred to as an MR inter-frame prediction model.

In the implementations presented herein, a low-resolution first plane image is generated for each scanning plane, which is then used to generate a high-resolution second plane image. The second plane image contains the same content as the first plane image, but has a higher resolution and a higher quality, which may serve as a high-quality final imaging for each scanning plane.

The method for MRI scanning proposed in the present disclosure obtains the original k-space data for the current scanning plane of the current scanning plane segment obtained by utilizing one of the at least two under-sampling factors, generates the first plane image corresponding to the current scanning plane, and then determines the type of the current scanning plane. Based on the type of the current scanning plane, a corresponding prediction mode is utilized to predict the second plane image of the current scanning plane based on the first plane image of the current scanning plane, thereby effectively shortening scanning time and improving scanning efficiency, meanwhile guaranteeing imaging quality.

Furthermore, if the current scanning plane is determined not to be the first type of scanning plane, the second plane image of the neighboring scanning plane corresponding to the current scanning plane is obtained, and based on the first plane image of the current scanning plane and the second plane image of the neighboring scanning plane, the second plane image corresponding to the current scanning plane is generated.

In the present disclosure, a low-resolution first plane image is first obtained for each scanning plane and then processed to obtain a high-resolution second plane image, effectively shortening the imaging time. By utilizing the structural correlation between neighboring plane images, generation of the predicted second plane images for the scanning planes is achieved, effectively reducing the scanning time. Separate scanning imaging is performed for different scanning planes in the scanning plane segment, ensuring image quality, and achieving the goal of high-speed, high-quality scanning and imaging for MRI.

On the basis of the above implementations, the generation of second plane image for the first type of scanning plane is further illustrated in conjunction with FIG. 2. FIG. 2 is a schematic flowchart of another implementation of the method for MRI scanning provided in the present disclosure.

At S201, in a case that the current scanning plane is of the first type, MR intra-frame imaging is performed for the current scanning plane based on the first plane image of the current scanning plane, and the second plane image of the current scanning plane is generated.

In general, for the first type of scanning plane, as there is no preceding neighboring scanning plane thereof, and the corresponding second plane image serves as the basis for imaging prediction of subsequent scanning planes, it is essential to ensure the correctness of the second plane image corresponding to the scanning plane of the first type.

By obtaining image data corresponding to the current scanning plane from the original k-space data, the first plane image of the current scanning plane can be generated. In some implementations, an MR intra-frame imaging model may be used to generate the second plane image of the current scanning plane. As shown in FIG. 3A, the first plane image of the current scanning plane is input into a pre-set first deep convolutional neural network (CNN) 301 for image feature extraction, and a feature image of the first plane image is acquired. The obtained feature image is then input into the first data processing model with the DC calculation architecture, shown as DC architecture 302 in FIG. 3A for example, and k-space data replacement is performed. The plane image obtained after the k-space data replacement is input into a second deep CNN 303 for residual processing, and residual information is output. The residual information is then combined with the resolution-enhanced plane image output by the DC architecture to generate the second plane image of the current scanning plane.

The DC architecture 302 operates in an example manner shown in FIG. 3B. The feature image of the first plane image is input into the DC architecture 302. The DC architecture 302 performs data conversion processing on the input feature image, for example, the feature image is converted into image data through Fourier transform (FFT) at 3021. The image data obtained through the image conversion processing is in the same format as the image data acquired by scanning and stored in the k-space. Furthermore, at 3022, at least a portion of the image data of the current scanning plane in the k-space acquired by scanning is utilized to replace the image data obtained by the image conversion processing, so as to obtain replaced k-space data of the current scanning plane, where a portion of the image data of the current scanning plane belonging to the first plane image acquired by scanning is stored in the k-space, and the data volume of this portion of image data is determined by the sampling rate of the first type of scanning plane, i.e., the first under-sampling factor. At 3023, the k-space data after the replacement is converted to the plane image through inverse Fourier transform (IFFT), and obtained plane image is output by the DC architecture 302.

It should be noted that, depending on the apparatus performing the MR scanning and requirements for the resolution of MR imaging, the processing procedure described above can be performed multiple times until the resolution of a final output image meets the requirements.

In the method for MRI scanning provided in the present disclosure, the resolution of the first plane image of the first type of scanning plane is enhanced through the MR intra-frame imaging model, ensuring the imaging quality and accuracy of the first type of scanning plane, and guaranteeing the effectiveness of subsequent imaging prediction that relies on the second plane image of the first type of scanning plane.

The acquisition of the second plane image for the non-first type of scanning plane in the above implementations is further illustrated in conjunction with FIG. 4 to FIG. 9.

At S401, the neighboring scanning plane corresponding to the current scanning plane is determined, and a second plane image of the neighboring scanning plane is acquired.

The neighboring scanning plane corresponding to the current scanning plane includes one or more scanning planes whose second plane images are obtained, and is near the current scanning plane in terms of scanning position and/or scanning order. The neighboring scanning plane may be in the same scanning plane segment as the current scanning plane.

There are various manners for determining the neighboring scanning plane corresponding to the current scanning plane. In some implementations, the neighboring scanning plane corresponding to the current scanning plane may be determined based on the sequential number of the scanning planes in the scanning plane segment, or based on the order of the scanning planes in the scanning plane segment. For instance, the current scanning plane segment includes at least one scanning plane of the first type and at least one scanning plane of the second type, if the current scanning plane is numbered 3, then a scanning plane numbered 2 may be determined as the neighboring scanning plane corresponding to the current scanning plane. For another instance, the neighboring scanning plane corresponding to the current scanning plane may be determined by checking if there is other scanning plane between the current scanning plane and a preceding scanning plane. If there is no other scanning plane between the preceding scanning plane and the current scanning plane, the preceding scanning plane may be determined as the neighboring scanning plane corresponding to the current scanning plane.

In some implementations, the neighboring scanning plane corresponding to the current scanning plane may be determined based on corresponding scanning positions of the body part. For example, a scanning plane corresponding to a scanning position near to that of the current scanning plane may be determined as the neighboring scanning plane corresponding to the current scanning plane.

In some implementations, the neighboring scanning plane corresponding to the current scanning plane may be determined based on the under-sampling factors associated with the scanning planes, or based on the types of the scanning planes. For example, a neighboring scanning plane with a lower under-sampling factor than that of the current scanning plane may be determined as the neighboring scanning plane corresponding to the current scanning plane. For another example, a neighboring scanning plane with an under-sampling factor no more than that of the current scanning plane may be determined as the neighboring scanning plane corresponding to the current scanning plane. For another example, a neighboring scanning plane of the first type or the second type may be determined as the neighboring scanning plane corresponding to the current scanning plane.

In some implementations, at least two of the above-mentioned manners may be used together to determine the neighboring scanning plane corresponding to the current scanning plane. For example, the neighboring scanning plane corresponding to the current scanning plane may be determined based on the positions of the scanning planes in the current scanning plane segment or their corresponding scanning positions, as well as on the types of scanning planes or the associated under-sampling factors. No limitation is set herein.

In some implementations, the MR inter-frame prediction mode includes a unidirectional inter-frame prediction mode and a bidirectional inter-frame prediction mode. In the unidirectional inter-frame prediction mode, a forward reference scanning plane is used to carry out the image prediction of the current scanning plane. In the bidirectional inter-frame prediction mode, a forward reference scanning plane and a backward reference scanning plane are used to carry out the image prediction of the current scanning plane. In this case, the neighboring scanning plane corresponding to the current scanning plane is determined based on the prediction mode of the current scanning plane or the type of the current scanning plane. In one example, if the prediction mode is the unidirectional inter-frame prediction mode, or the current scanning plane is the second type of scanning plane, a forward neighboring scanning plane is determined as the neighboring scanning plane corresponding to the current scanning plane. In another example, if the prediction mode is the unidirectional inter-frame prediction mode, or the current scanning plane is the third type of scanning plane, a forward neighboring scanning plane and a backward neighboring scanning plane are determined as the neighboring scanning plane corresponding to the current scanning plane. The forward neighboring scanning plane may be a scanning plane with an associated scanning position near to that of the current scanning plane along a first direction, and the backward neighboring scanning plane may be a scanning plane with an associated scanning position near to that of the current scanning plane along a second direction opposite to the first direction. The determination of the forward neighboring scanning plane and/or the backward neighboring scanning plane may refer to the above mentioned method, which is not repeated herein.

At S402, based on the first plane image of the current scanning plane and the second plane image of the neighboring scanning plane, imaging prediction for the current scanning plane is performed to generate the second plane image of the current scanning plane.

The first plane image of the current scanning plane and the second plane image of the neighboring scanning plane may be processed by the MR inter-frame model, to generate the second plane image of the current scanning image.

Figures 5, 6:
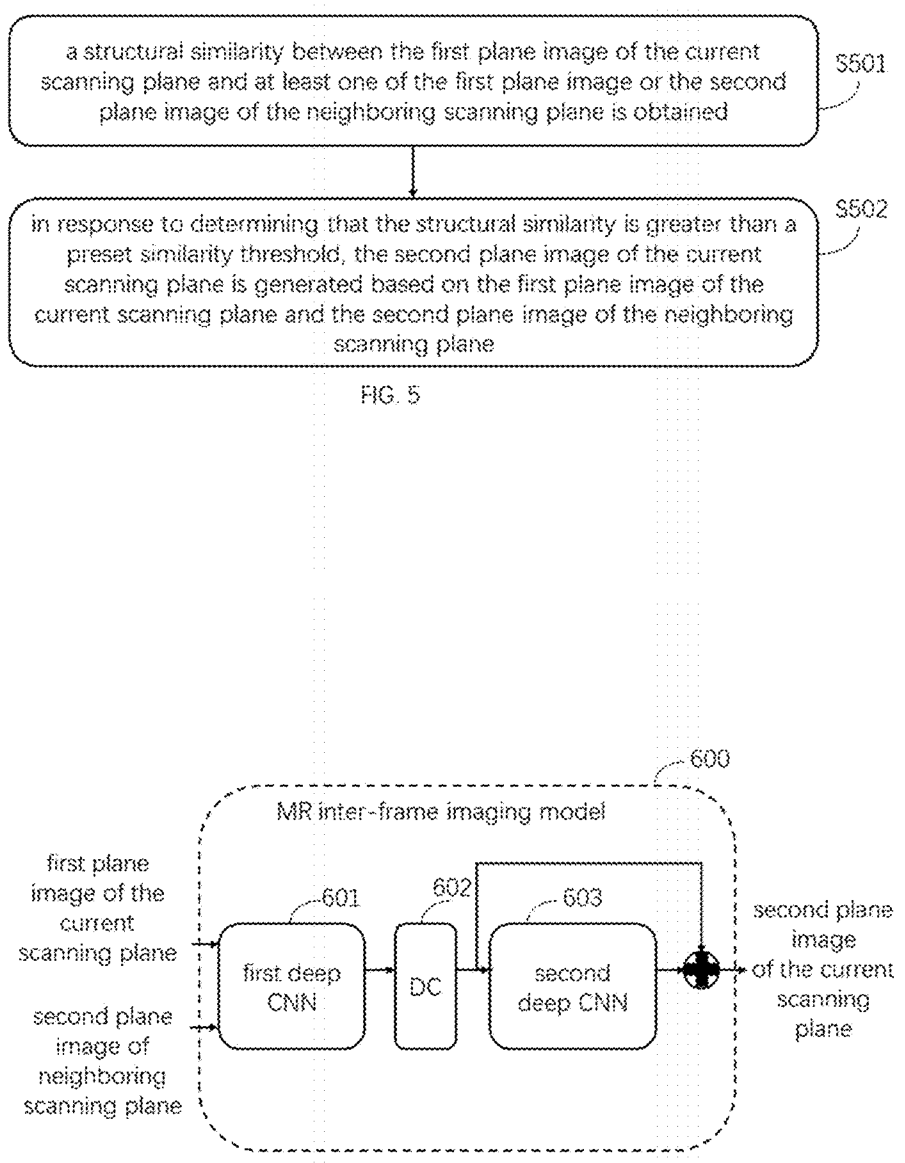
FIG. 5 is a schematic flowchart illustrating the method for MRI scanning in another implementation of the present disclosure.
FIG. 6 is a schematic flowchart illustrating an MR inter-frame prediction model in an implementation of the present disclosure.

FIG. 5 is a schematic flowchart of another implementation of the method for MRI scanning provided in this disclosure. As shown in FIG. 5, the method includes the following procedures.

At S501, a structural similarity between the first plane image of the current scanning plane and at least one of the first plane image or the second plane image of the neighboring scanning plane is obtained.

At S502, in response to determining that the structural similarity is greater than a preset similarity threshold, the second plane image of the current scanning plane is generated based on the first plane image of the current scanning plane and the second plane image of the neighboring scanning plane.

In the implementations of the present disclosure, the scanning planes included in the scanning plane segment can be divided into the first type of scanning plane and non-first type of scanning plane. The non-first type of scanning plane includes the second type of scanning plane, where the second type of scanning plane has a preceding neighboring scanning plane. The second type of scanning plane may correspond to an under-sampling factor closest to that of the first type of scanning plane. The imaging of the preceding neighboring scanning plane is completed and the second plane image of the preceding neighboring scanning plane is obtained.

For the current scanning plane of the second type or the third type, image prediction can be performed based on the structural correlation between the preceding neighboring scanning plane and the current scanning plane, and the second plane image of the current scanning plane is obtained by utilizing the second plane image of the preceding neighboring scanning plane. The second plane image of the current scanning plane of the second type can be obtained by the unidirectional inter-frame prediction mode.

Different scanning planes within the same scanning plane segment exhibit structural correlation, especially for two neighboring scanning planes of which the corresponding parts of the scanning objects are adjacent. Therefore, neighboring scanning planes have a stronger correlation, which can be expressed as a similarity between plane images.

After obtaining the first plane image of the current scanning plane, a similarity threshold can be set. If the structural similarity between the first plane image of the current scanning plane and the first plane image and/or the second plane image of the preceding neighboring scanning plane exceeds the preset similarity threshold, it can be determined that, the structure of the scanning object corresponding to the current scanning plane is similar to that of the preceding neighboring scanning plane, and no abnormal changes have occurred. Therefore, the predicted second plane image of the current scanning plane is considered reasonably valid.

Furthermore, based on the first plane image of the current scanning plane and the second plane image of the preceding neighboring scanning plane, a high-resolution and high-quality second plane image can be obtained. In some implementations, an image processing model, such as the MR inter-frame prediction model as shown in FIG. 6, can be used for resolution enhancement.

The MR inter-frame prediction model is similar to the MR intra-frame imaging model. Both the second plane image of the preceding neighboring scanning plane and the first plane image of the current scanning plane can be input into a designated first deep convolutional neural network 601 for feature extraction, obtaining a feature image. The obtained feature image can then be input into the DC calculation architecture 602 for k-space data replacement. The specific implementations of the k-space data replacement in the DC calculation architecture can refer to above descriptions, which will not be described herein.

Additionally, the resolution-enhanced image output by the DC architecture can be input into a designated second deep convolutional neural network 603 for residual processing, and residual information is output. A high-resolution second plane image is generated based on the residual information output by the second deep convolutional neural network and the resolution-enhanced image output by the DC architecture.

It should be noted that, the above processing can be carried out in multiple iterations depending on the specific requirements to achieve the desired standard for the second plane image.

The method for MRI scanning proposed in the implementations of this disclosure acquires, based on structural similarity, the first plane image of the current scanning plane through the prediction of the second plane image of the preceding neighboring scanning plane, and generates a higher-resolution second plane image of the current scanning plane. By acquiring the first plane image of the current plane by prediction, the imaging time is effectively reduced. By simultaneously processing the second plane image of the preceding neighboring scanning plane and the first plane image of the current scanning plane with the MR inter-frame prediction model, the accuracy and quality of imaging are ensured.

On the basis of the above implementations, the case that the structural similarity is less than or equal to the preset similarity threshold is illustrated in conjunction with FIG. 7. As shown in FIG. 7, the method includes the following procedures.

At S701, in the case that the structural similarity is less than or equal to the preset similarity threshold, move the current scanning plane to the next scanning plane segment.

On the basis of the above implementations, if the structural similarity between the first plane image of the current scanning plane and the first plane image and/or the second plane image of the preceding neighboring scanning plane is less than or equal to the preset similarity threshold, it indicates that the structural similarity between the current scanning plane and the preceding neighboring scanning plane is relatively low, and it can be determined that the structure of the scanning object corresponding to the current scanning plane undergoes a significant change compared to the structure of the scanning object corresponding the preceding neighboring scanning plane.

MRI imaging of the entire scanning object is based on a fusion of images generated from each scanning plane segment, and the final imaging of each scanning plane segment is based on a fusion of second plane images of all scanning planes within the scanning plane segment. Therefore, in the case that the structural similarity between the current scanning plane and the preceding neighboring scanning plane is less than the set similarity threshold, if the prediction of the second plane image of the current scanning plane is still predicted and constructed based on the second plane image of the preceding neighboring scanning plane, the predicted second plane image of the current scanning plane will not match the actual condition of the scanning object, the predicted second plane image of the current scanning plane does not correspond to the actual situation of the scanning object, resulting in inaccurate imaging results. Furthermore, if the imaging result of the current scanning plane is used to predict and construct the second plane image of the subsequent scanning plane, the imaging result of the subsequent scanning plane will also be inaccurate, which in turn affects the accuracy of the final imaging result of the current scanning plane segment to which the current scanning plane belongs.

Additionally, since the current scanning plane is in close proximity to the preceding neighboring scanning plane, a new scanning plane segment needs to be created for the part corresponding to the scanning object where changes are present, so as for a comprehensive imaging of the part, and the current scanning plane is put into the next scanning plane segment newly created.

In some implementations, the current scanning plane may be served as the initial scanning plane in the next scanning plane segment, i.e., the first type of scanning plane. Alternatively, the current scanning plane may be placed in a non-initial position within the next scanning plane segment, making it a non-first type of scanning plane.

In the case where the current scanning plane is taken as the initial scanning plane in the next scanning plane segment, the current scanning plane is the first type of scanning plane for the next scanning plane segment. By acquiring its corresponding k-space data, the first plane image can be generated, and subsequent imaging predictions can be performed to obtain the corresponding second plane image. In the case where the current scanning plane is placed in a non-initial position in the next scanning plane segment, the current scanning plane is the non-first type of scanning plane of the next scanning plane segment, a neighboring scanning plane may be scanned and imaged as the first type of scanning plane for the next scanning plane segment, so as to obtain the second plane image of the neighboring scanning plane, and the operation of obtaining relevant plane images can be carried out when it is the turn for imaging the current scanning plane in the next scanning plane segment.

The method for MRI scanning provided in the implementations of this disclosure addresses the situation where a similarity of the first plane image of the current scanning plane and the second plane image of the preceding neighboring scanning plane is less than or equal to the preset similarity threshold, and provides an appropriate processing method that allows for adjustments of the MRI scanning process in time based on changes in actual conditions, enabling focused imaging on the area of the scanning object that undergoes changes, which improves the accuracy of MRI imaging and enhances the usability of the imaging results.

Furthermore, as illustrated in FIG. 8, the present disclosure provides another implementation of the method for MRI scanning. The method includes the following procedures.

At S801, in the case that the structural similarity is less than or equal to the preset similarity threshold, at least one of the k-space data or the first plane image of the current scanning plane is saved.

In some implementations, scanning image data acquired in the process of MRI scanning or prediction is stored in the k-space, so as to reduce the time required for data retrieval. Similarly, the image data predicted for the first plane image of a particular scanning plane is also stored. In the subsequent process of acquiring plane images by scanning and/or prediction, in the event of image data acquisition for the same scanning plane, the previously saved data can be directly accessed, thereby effectively reducing the data retrieval time.

In some implementations, if the structural similarity between the second plane image of the preceding neighboring scanning plane and the first plane image of the current scanning plane is less than or equal to the preset similarity threshold, it can be determined that an abnormal situation occurs in the prediction of the second plane image of the current scanning plane, such as, for example, the clarity of the second plane image is low. In this scenario, the image data obtained by scanning the current scanning plane is stored in k-space, and the first plane image obtained based on the original k-space data is stored at a designated location.

Furthermore, the current scanning plane may be removed from the current scanning plane segment and added to the next scanning plane segment.

In some implementations, the current scanning plane may become one of the scanning planes in the next scanning plane segment, and when it is time to perform the scanning and imaging prediction for the current scanning plane in the next scanning plane segment, if the current scanning plane is not the first type of scanning plane of the next scanning plane segment, the saved first plane image can be directly used as the first plane image of the current scanning plane, thus avoiding to perform the scanning again for the current scanning plane.

In some implementations of the present disclosure, in the case that the current scanning plane belongs to the non-first type of scanning plane in the next scanning plane segment, the saved historical image data may be directly used to generate the first plane image during the imaging of the current scanning plane.

Typically, the first plane image of the non-first type of scanning plane is generated based on the original k-space data of the current scanning plane, and subsequent imaging is performed based on the similarity between the first plane image of the current scanning plane and the second plane image of its preceding neighboring scanning plane. Therefore, in the presence of stored historical image of the current scanning plane, the stored historical plane image data may be directly accessed, and the first plane image of the current scanning plane may be generated based on the historical plane image data. By accessing the historical data, the generation time of the first plane image can be reduced while ensuring its accuracy. Alternatively, the stored first plane image may be directly accessed and used as the first plane image of the current scanning plane, which further reduces the generation time of the first plane image.

In an alternative implementation, the current scanning plane may become the initial scanning plane in the next scanning plane segment, i.e., the current scanning plane is taken as the first type of scanning plane in the next scanning plane segment. In this case, supplementary acquisition of the original k-space data is performed according to a sampling rate corresponding to the first type of scanning plane, and the first plane image of the current scanning plane is generated based on the k-space data obtained after the supplementary acquisition.

In the present disclosure, k-space stores image data of the scanning plane on which the scanning and sampling is performed, and the first plane image of the scanning plane of the first type may be generated by obtaining image data from the k-space. Furthermore, in the case where the scanning plane belongs to the first type of scanning plane, the generation of its first plane image requires more sampling image data of the scanning plane than that for the non-first type of scanning plane.

Because under-sampling is performed for the scanning planes, and the first type of scanning plane corresponds to a smaller under-sampling factor and a greater sampling rate than that of the non-first type of scanning plane, the historical image data stored in the k-space is just a portion of image data obtained by scanning and sampling the scanning plane, and the amount of data thereof is determined by the sampling rate of the scanning plane corresponding to its type in the current scanning plane segment. In the case where the scanning plane belongs to the first type of scanning plane in the next scanning plane segment, it is necessary to carry out supplementary acquisition of the image data for the unsampled portion of the scanning plane, thereby obtaining adequate image data for the scanning plane to perform intra-frame imaging.

It should be noted that, to ensure consistency between the format of the image data obtained by the supplementary sampling and that of the historical data stored in k-space, the sampling rate during the supplementary sampling of the image data can be adjusted to be consistent with the sampling rate of the first type of scanning plane.

Furthermore, after the completion of supplementary sampling, more image data for the scanning plane is stored in the k-space, allowing the generation of the second plane image of the scanning plane based on the k-space data.

In the method for MRI scanning disclosed herein, in the case that the structural similarity between the first plane image of the current scanning plane and the second plane image of the preceding neighboring scanning plane falls below the preset similarity threshold, a solution is proposed for handling situations where the current scanning plane is located in different positions in the next scanning plane segment, effectively reducing the time required for MR scanning and imaging while ensuring imaging accuracy.

FIG. 9 illustrates a schematic flowchart of another implementation of the method for MRI scanning disclosed herein, which includes S901 and S902. In the implementation, the current scanning plane is the non-first type of scanning plane.

At S901, a prediction mode for the current scanning plane is obtained, where the inter-frame prediction mode includes a unidirectional inter-frame prediction mode or a bidirectional inter-frame prediction mode.

In the unidirectional inter-frame prediction, the second plane image of the current scanning plane is predicted based on the second plane image of the preceding forward neighboring scanning plane corresponding to the current scanning plane and on the structural similarity between the current scanning plane and its preceding neighboring scanning plane.

In the bidirectional inter-frame prediction, the second plane image of the current scanning plane is predicted based on the second plane image of the current scanning plane as well as the second plane image of its preceding forward neighboring scanning plane and the second plane image of its preceding backward neighboring scanning plane, so as to obtain the second plane image of the current scanning plane.

In the implementations of the present disclosure, a desired prediction mode can be determined based on the type of scanning plane of which plane image is to be predicted.

Typically, in order to enhance the imaging quality for each scanning plane segment, plane images are generated as many as possible for each scanning segment. By merging the plane images corresponding to multiple scanning planes, high-quality MR scanning images can be output for corresponding scanning plane segments.

In some implementations, the unidirectional inter-frame prediction is used to predict the second plane image of the current scanning plane based on the second plane image of its preceding neighboring scanning plane.

In some implementations, the bidirectional inter-frame prediction is employed to generate the second plane image the current scanning plane based on both the second plane images of the forward and backward preceding neighboring scanning planes and the first plane image of the current scanning plane.

Figure 10:
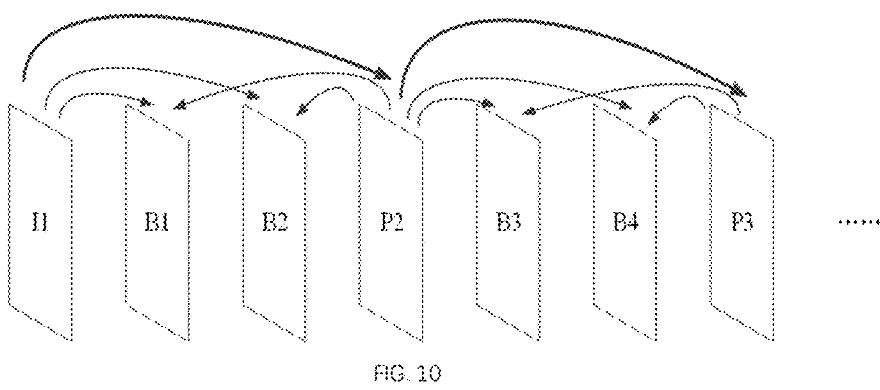
FIG. 10 is a schematic flowchart illustrating the method for MRI scanning in another implementation of the present disclosure.

As shown in FIG. 10, assuming the first type of scan planes are collectively referred to as the plane I, the second type of scanning planes are collectively referred to as plane P, and the third type of scanning planes are collectively referred to as plane B. In the current scanning plane segment, scanning and imaging is performed in the following order: plane I, followed by plane P, and then plane B, where the scanning position of the plane B is between the scanning positions of two neighboring planes P or neighboring plane I and plan P. The scanning may be performed for one or more iterations based on the order. In the example shown in FIG. 10, the current scanning plane segment includes one first type of scanning plane, I1, two second type of scanning planes, P1 and P2, and four third type of scanning planes, B1, B2, B3 and B4, and the scanning planes are scanned sequentially in the order of I1, P2, B1, B2, P3, B3, and B4. The scanning planes shown in FIG. 10 are ranked according to their corresponding scanning positions. In some other implementations, for a scanning position between the scanning positions of the plane I and plane P, one or more planes P may be scanned. In some other implementations, more than one plane I may be included in the current scanning plane segment, and one or more planes P may be scanned on positions between the scanning positions of two neighboring planes I. No specific limitations are imposed herein.

The scanning plane I1 is of the first type in the current scanning plane segment, and the second plane image of the scanning plane I1 may be obtained based on the original k-space data of the scanning plane I1. In an example, the original k-space data of the scanning plane I1 is processed by inverse Fourier transform to obtain the first plane image of the scanning plane I1, and the first plane image of the scanning plane I1 is input into the intra-frame imaging model for processing, to obtain the second plane image of the scanning plane I1.

The scanning plane P2 is then scanned to obtain the original k-space data. The scanning plane P2 is of the second type, and the imaging prediction of the scanning plane P2 is performed in the unidirectional inter-frame prediction mode, where the scanning plane I1 is served as the forward neighboring scanning plane of the scanning plane P2. In an example, the original k-space data of the scanning plane P2 is processed by inverse Fourier transform to obtain the first plane image of the scanning plane P2, and the first plane image of the scanning plane P2 as well as the second plane image of the scanning plane I1 are input into the inter-frame prediction model for processing, to obtain the second plane image of the scanning plane P2.

The scanning planes B1 and B2 are then scanned sequentially or in parallel to obtain the original k-space data. The scanning planes B1 and B2 are of the third type, and the imaging prediction of the scanning planes B1 and B2 are performed in the bidirectional inter-frame prediction mode, where the scanning plane I1 is served as the forward neighboring scanning plane of the scanning planes B1 and B2, and the scanning plane P2 is served as the backward neighboring scanning plane of the scanning planes B1 and B2. In an example, the original k-space data of the scanning plane B1 or B2 is processed by inverse Fourier transform to obtain the first plane image of the scanning plane B1 or B2, and the first plane image of the scanning plane B1 or B2 as well as the second plane images of the scanning planes I1 and P2 are input into the inter-frame prediction model for processing, to obtain the second plane image of the scanning plane B1 or B2.

Subsequently, the scanning plane P3 is scanned, and the imaging prediction of the scanning plane P3 is performed in the unidirectional inter-frame prediction mode, where the scanning plane P2 is served as the forward neighboring scanning plane of the scanning plane P3. Finally, the scanning planes B3 and B4 are scanned, and the imaging prediction of the scanning planes B3 and B4 are performed in the bidirectional inter-frame prediction mode, where the scanning plane P2 is served as the forward neighboring scanning plane of the scanning planes B3 and B4, and the scanning plane P3 is served as the backward neighboring scanning plane of the scanning planes B3 and B4.

It should be noted that B1, B2, B3, and B4 are provided as examples. In practice, the number of plane images between two second type of neighboring scanning planes can be more than two, and is not limited herein.

At S902, based on the prediction mode, a preceding scanning plane of the first or the second type is determined as the neighboring scanning plane corresponding to the current scanning plane.

The unidirectional inter-frame prediction is realized based on the plane image of the forward neighboring scanning plane. The bidirectional inter-frame prediction is realized based on the plane images of two neighboring scanning planes which are the forward and the backward of the current scanning plane in terms of corresponding scanning positions.

In some implementations, in the case that the prediction mode is the unidirectional inter-frame prediction mode, the preceding predicted scanning plane of the current scanning plane is determined as the neighboring scanning plane.

As illustrated in FIG. 10, the second plane image of the scanning plane P2 is generated by the unidirectional inter-frame prediction based on the second plane image of the scanning plane I1, and the second plane image of the scanning plane P3 is generated by the unidirectional inter-frame prediction based on the second plane image of the scanning plane P2. That is, the scanning plane I1 is the forward predicted scanning plane of the scanning plane P2, and the scanning plane I1 is determined as the neighboring scanning plane corresponding to the scanning plane P2. Similarly, the scanning plane P2 is the forward predicted scanning plane of the scanning plane P3, and the scanning plane P2 is determined as the neighboring scanning plane corresponding to the scanning plane P3.

In some implementations, in the case that the prediction mode is the bidirectional inter-frame prediction mode, both the forward predicted scanning plane and the backward predicted scanning plane of the current scanning plane are determined as the neighboring scanning plane corresponding to the current scanning plane.

As shown in FIG. 10, the second plane images of the scanning planes B1 and B2 are generated through the bidirectional inter-frame prediction based on the plane images of the scanning planes I1 and P2. It can be known from the illustrated order in FIG. 10 that, the scanning plane I1 is the forward predicted scanning plane of the scanning planes B1 and B2, and P2 is the backward predicted scanning plane of the scanning planes B1 and B2. Therefore, the scanning planes I1 and P2 can be determined as the neighboring scanning plane corresponding to both the scanning planes B1 and B2. It can be known from the illustrated order that, P2 is the forward predicted scanning plane of the scanning planes B3 and B4, and P3 is the backward predicted scanning plane of the scanning planes B3 and B4. Thus, the scanning planes P2 and P3 can be determined as the neighboring scanning plane corresponding to both the scanning planes B3 and B4.

In the above example, one or more scanning planes of the first type or the second type closest to the current scanning plane in terms of scanning positions are determined as the neighboring scanning plane corresponding to the current scanning plane. The neighboring scanning plane corresponding to the current scanning plane may be of the first type or the second type, and imaging prediction is completed for the neighboring scanning plane. The neighboring scanning plane may be adjacent to the current scanning plane in terms of the scanning positions, but the present disclosure is limited thereto.

In some implementations, after determining the neighboring scanning plane corresponding to the current scanning plane, a similarity between the first plane image of the current scanning plane and the first and/or second plane image of the corresponding neighboring scanning plane may be determined, and subsequent unidirectional inter-frame prediction is performed only in the case that the similarity is relatively high, such as, for example, the similarity is greater than the similarity threshold. Taking the scanning plane P2 as an example, if the similarity between the first plane image of scanning plane P2 and the first and/or second plane image of its neighboring scanning plane I1 is less than the predetermined similarity threshold, the scanning plane P2 is removed from the current scanning plane segment, and added to a new scanning plane segment. In this case, the current scanning plane segment may include the scanning plane I1 only. Furthermore, at least one of the original k-space data or the first plane image of the scanning plane P2 may be saved for use in another imaging procedure of the scanning plane P2.

The scanning plane P2 may be taken as the first type of scanning plane in the next scanning level segment. In this case, the scanning plane P2 is adjusted to the scanning plane 12, and supplementary sampling of the original k-space data of the scanning plane 12 may be performed based on the first under-sampling factor, and the k-space data acquired in the supplementary sampling and the original k-space data may be utilized to re-generate the first plane image of the scanning plane 12, and the second plane image of the scanning plane 12 is generated based on the first plane image and the intra-frame imaging model.

Alternatively, the scanning plane P2 may be taken as the non-first first of scanning plane in the next scanning level segment. In this case, the scanning plane B1, which is supposed to be scanned with the third under-sampling factor, is adjusted to be the first type of the scanning plane in the next scanning plane segment, i.e., the scanning plane 12. The first under-sampling factor is utilized for scanning of the scanning plane 12 and the second image plane of the scanning plane 12 is generated. Then, when it is the turn to scan the scanning plane P2, since the first plane image of the scanning plane P2 or the original k-space data is stored, the stored first plane image or the original k-space data may be directly taken to obtain the first plane image of the scanning plane P2, without performing the scanning again for the scanning plane P2.

In some implementations, the bidirectional inter-frame prediction may be performed only when the structural similarity between the plane images of the current scanning plane and the neighboring scanning plane exceeds the predefined similarity threshold. In FIG. 10, the bidirectional inter-frame prediction is performed based on the second plane images of the scanning planes I1 and P2 to generate the second plane image of the scanning planes B1 or B2 only in the case that the similarity between the first or second plane images of the scanning planes P2 and I1 and the first plane image of the scanning plane B1 or B2 exceeds the predefined threshold. Alternatively, the bidirectional inter-frame prediction is performed based on the second plane images of the scanning planes P2 and P3 to generate the second plane image of the scanning plane B3 or B4 only in the case where the similarity between the first or second plane images of P3 and P2 and the first plane image of the scanning plane B3 or B4 exceeds the predefined threshold.

In some implementations, a network model for the MR inter-frame prediction mode can be used to generate high-resolution second plane images of the scanning planes corresponding to B1, B2, B3, and B4.

The network model may be the MR inter-frame prediction model described above. In the bidirectional inter-frame prediction mode, for more accurate resolution enhancement, the low-resolution first plane image of the current scanning plane and the second plane images of the two neighboring scanning planes are simultaneously input into a designated first deep convolutional neural network for image feature extraction, so as to generate one or more feature images as output. Furthermore, the one or more feature images output from the first deep convolutional neural network are input into a DC calculation architecture for k-space data replacement. The plane image obtained after the k-space data replacement is then input into a designated second deep convolutional neural network for residual processing, and residual information is output. The residual information output from the second deep convolutional neural network is merged with the resolution-enhanced plane image output by the DC architecture to generate the corresponding second plane image.

The method for MRI scanning provided in the implementations of this disclosure addresses the requirements for plane images of different scanning planes, and acquires the second plane images of the scanning planes in different inter-frame prediction manners, effectively reducing scanning and imaging time for MRI while ensuring image quality.

Furthermore, as shown in FIG. 12, FIG. 12 illustrates another implementation of the method for MRI scanning disclosed herein, in which the inter-frame prediction is performed for the current scanning plane.

At S1201, in the case where the current scanning plane is a plane set including a plurality of sub-scanning planes, starting from the initial sub-scanning plane in the plane set, an MR inter-frame prediction is performed for each sub-scanning plane in the plane set to generate a second plane image corresponding to the sub-scanning plane. This process continues until imaging of all the sub-scanning planes in the plane set is completed, and the method proceeds to the next scanning plane or the next scanning plane segment.

In some implementations of the present disclosure, the current scanning plane can include a single scanning plane. Alternatively, the current scanning plane can include multiple scanning sub-planes, which are combined to generate the current scanning plane.

For the case where the current scanning plane contains a plurality of sub-scanning planes, imaging is performed for all of the sub-scanning planes sequentially according to the scanning order. For each current sub-scanning plane, unidirectional inter-frame prediction is carried out based on the first or second plane image of the neighboring sub-scanning plane to obtain the second plane image of the current sub-scanning plane. This process is repeatedly performed for all sub-scanning planes until second plane images of all the sub-scanning planes are obtained, and the imaging of the current scanning plane is completed.

In the case where the current scanning plane is the last scanning plane in its corresponding scanning plane segment, after completing the imaging of the current scanning plane, the method proceeds to the next scanning plane segment and begins imaging of the initial scanning plane of the next scanning plane segment as well as subsequent operations. In the case where the current scanning plane is not the last one in its corresponding scanning plane segment, after completing the imaging of the current scanning plane, the method proceeds to the next scanning plane and obtains the first plane image of the next scanning plane.

In the method for MRI scanning provided in the implementations of this disclosure, if the scanning plane segment includes multiple scanning planes, or if the scanning plane includes multiple sub-scanning planes, the plane images are generated sequentially, ensuring high-quality presentation of the plane images which are finally output.

In some implementations, the acquisition of the second plane image of the current scanning plane is further illustrated in conjunction with FIG. 13. FIG. 13 illustrates another implementation of the method for MRI scanning disclosed herein.

At S1301, feature extraction is performed on the input plane image by a feature extraction layer, and a feature image is output. In the case of the MR inter-frame prediction, the input plane image is the first plane image of the current scanning plane and the second plane image of the neighboring scanning plane. In the case of the MR intra-frame imaging, the input plane image is the first plane image of the current scanning plane.

Typically, the second plane image is obtained by resolution enhancement based on the first plane image. In some implementations of this disclosure, the first plane image is input to the feature extraction layer, such as a designated first deep convolutional neural network, for feature extraction, and corresponding feature image is generated.

Distinct feature extraction processes are set in the feature extraction layer for the first plane images of different types of scanning planes, allowing for image feature extraction of the first plane images for different types of scanning planes.

For instance, for the initial scanning plane of the first type in the scanning plane segment, the first plane image of the scanning plane may be generated based on image data stored in k-space. The first plane image is then subjected to resolution enhancement using an MR intra-frame prediction model, ultimately generating the second plane image of the scanning plane. In the MR intra-frame imaging model, the feature extraction layer may be the designated first deep convolutional neural network, thus enabling independent processing of the first plane image.

For another instance, in the case that the current scanning plane is not of the first type, the first plane image of the current scanning plane may be obtained by unidirectional inter-frame prediction based on the second plane image of the forward neighboring scanning plane. Alternatively, the second plane image of the current scanning plane may be acquired by bidirectional inter-frame prediction based on the second plane image of the forward neighboring scanning plane and the second plane image of the backward neighboring scanning plane. The second plane image of the current scanning plane, obtained by the unidirectional and/or bidirectional inter-frame prediction, has a resolution higher than that of the first plane image, realizing image resolution enhancement for the current scanning plane.

In the case that the second plane image of the scanning plane is acquired by the unidirectional inter-frame prediction, both the second plane image of the forward neighboring scanning plane and the first plane image of the current scanning plane may be simultaneously input into the MR inter-frame prediction model. The feature extraction layer in the MR inter-frame prediction model may extract features from both plane images simultaneously and merge the extracted features, so as to generate one or more feature images corresponding to the first plane image.

In the case that the second plane image of the scanning plane is acquired by the bi-directional inter-frame prediction, the second plane image of the forward neighboring scanning plane, the second plane image of the backward neighboring scanning plane, as well as the first plane image of the current scanning plane are simultaneously input into the MR inter-frame prediction model. The feature extraction layer in the MR inter-frame prediction model can extract features from all three plane images simultaneously and merge the extracted features, so as to generate one or more feature images corresponding to the first plane image.

At S1302, a data processing layer generates predicted k-space data for the feature image, and generates a predicted enhancement plane image of the current scanning plane based on the predicted k-space data.

In the implementation, both the MR intra-frame imaging model and the MR inter-frame prediction model are provided with the data processing layer. The input of the data processing layer is the output of the feature extraction layer, and k-space data replacement is implemented through the data processing layer.

The data processing layer may have a DC calculation architecture. In the DC architecture, Fourier transform is carried out on the feature image to obtain corresponding image data. The transformed image data is compared with the image data stored in k-space, and a portion of the transformed image data which can be covered with the image data stored in k-space is replaced. Finally, the replaced image data is transformed by inverse Fourier transform to generate the enhanced plane image.

The portion of predicted k-space data at the sampling rate, i.e., corresponding sampled k-space data exists, is replaced with the original k-space data to generate the target k-space data.

In some implementations, the image data in k-space is mostly acquired based on sampling, and the image data stored in the k-space is only a portion of the image data of the scanning plane based on the sampling rate. Meanwhile, the second plane image of the current scanning plane, generated by prediction based on the second plane image of the neighboring scanning plane, carries all the image data of the current scanning plane.

Therefore, to improve the accuracy of the second plane image of the current scanning plane, the portion of predicted image data can be replaced with the image data stored in k-space and obtained by sampling, where the replaced image data is the image data in all the predicted image data at the same position as that stored in k-space, so as to generate the target k-space data.

Figures 14, 15:
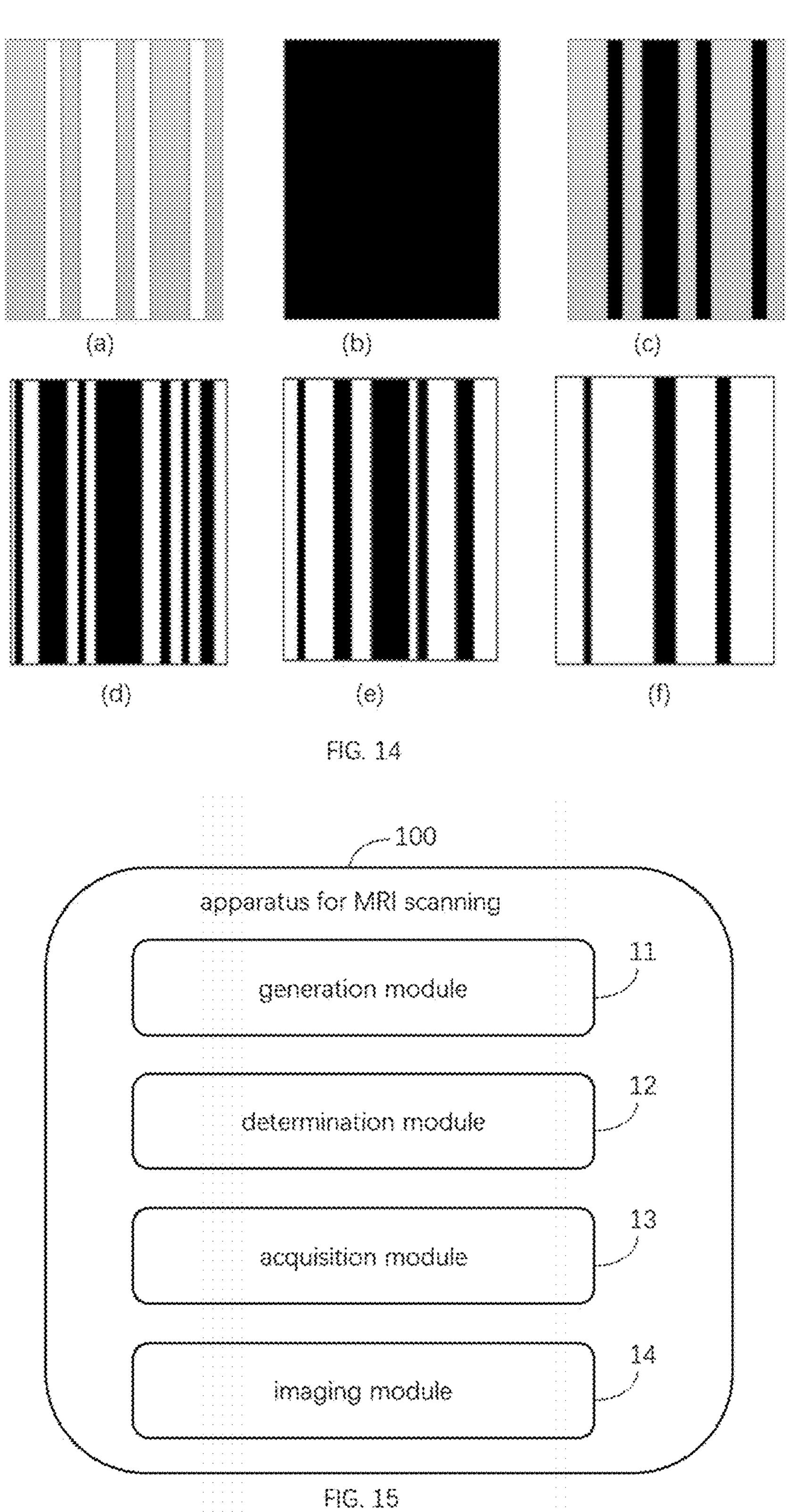
FIG. 14 is a schematic flowchart illustrating the method for MRI scanning in another implementation of the present disclosure.
FIG. 15 is a schematic structural diagram illustrating an apparatus for MRI scanning in an implementation of the present disclosure.

As shown in section (a) of FIG. 14, the gray portion can be understood as the image data of the current scanning plane that is scanned, sampled, and stored in k-space, from which the first plane image of the current scanning plane is generated. Due to the presence of an under-sampling factor in the scanning, only a portion of the image data of the current scanning plane is acquired, and the white area represents the blank space where no image data has been sampled. The section (b) of FIG. 14 illustrates the predicted image data represented by the black area. Furthermore, the image data in the predicted image data which is at the same position in section (b) as the gray portion in section (a) is replaced by the corresponding original k-space data, such that the target k-space data of the current scanning plane is generated, as shown in section (c) of FIG. 14. The target k-space data includes the dark portion representing the predicted image data and the gray portion representing the original image data.

In some implementations, one or more scanning templates may be utilized for under-sampling of respective scanning planes, where the horizontal axis represents the frequency, and the vertical axis represents the phase. Three scanning samples are shown in sections (d), (e) and (f) of FIG. 14. From the section (d) to section (f) of FIG. 14, the corresponding under-sampling factor increases gradually, leading to a decrease in the corresponding sampling rate, and as a result, the acquired image data by scanning becomes sparser. As an example, sections (d), (e) and (f) may be scanning templates with 4× under-sampling, 8× under-sampling, and 16× under-sampling, respectively, but the present disclosure is not limited hereto. In the example under-sampling templates, the low frequency portion in the central region is completely sampled, and the high frequency portion in the surrounding region is randomly sampled, where the frequency points that are sampled using the three under-sampling factors respectively may partially overlap or may be complementary.

Furthermore, a predicted enhancement plane image of the current scanning plane is generated based on the target k-space data.

In some implementations of the present disclosure, after replacing the k-space data, the accuracy of the obtained target k-space data is higher, which allows for the generation of a plane image with a higher resolution than the input feature image based on the image data with a higher accuracy, i.e., the predicted enhancement plane image of the current scanning plane.

At S1303, the predicted enhancement plane image is input into an image enhancement layer, and residual information is output. The second plane image of the current scanning plane is generated based on the residual information and the predicted enhancement plane image.

The predicted enhancement plane image may be input into the image enhancement layer, where the image enhancement layer may be a second deep neural network. The second deep neural network performs residual processing on the input image and outputs residual of the enhancement information. Furthermore, the residual of the enhancement information is fused with the input plane image of the second deep neural network to generate the second plane image of the current scanning plane.

Figure 11:
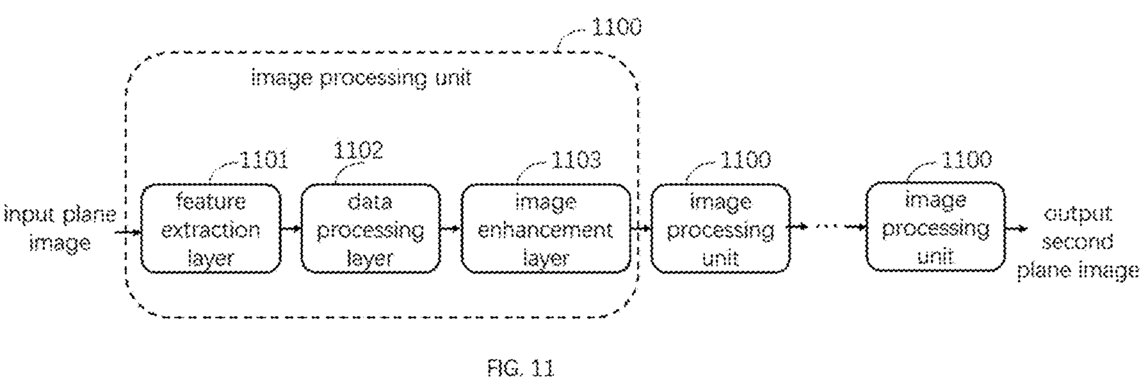
FIG. 11 is a schematic flowchart illustrating a universal architecture of the MR intra-frame imaging model and the MR inter-frame prediction model in an implementation of the present disclosure.

In some implementations, in the MR intra-frame imaging mode, the imaging prediction is performed by the MR intra-frame imaging model, and in the MR inter-frame prediction mode, the imaging prediction is performed by the MR inter-frame prediction model. Optionally, the MR inter-frame imaging model and the MR intra-frame prediction model may be realized with a universal architecture. As shown in FIG. 11, both models include one or more image processing units 1100 that are connected sequentially. Each image processing unit includes a feature extraction layer 1101, a data processing layer 1102, and an image enhancement layer 1103. The feature extraction layer 1101, the data processing layer 1102, and the image enhancement layer 1103 in each image processing unit 1100 are connected in sequence, and the output of the image enhancement layer 1103 is the input of the feature extraction layer 1101 of the next image processing unit 1100.

The number of image processing units contained in the MR inter-frame prediction model and the MR intra-frame imaging model can be manually set based on the resolution requirements on the second plane image of the scanning plane, or be determined based on relevant parameters of the apparatus for MRI scanning. In some implementations, the feature extraction layer 1101 may be the first deep CNN, the data processing layer 1102 may be the DC architecture, and the image enhancement layer 1103 may be the second deep CNN, but the present disclosure is not limited thereto.

In some implementations, rather than inputting the first plane image of the current scanning plane into the intra-frame imaging model or the inter-frame prediction model, the original k-space data of the current scanning plane may be input into the model for processing and the model may generate the first plane image of the current scanning plane based on the original k-space data. Alternatively, both the original k-space data and the first plane image of the current scanning plane are input into the model for processing, which is not limited by the present disclosure.

It should be noted that, in addition to the above implementations of the method for enhancing the resolution of the first plane image of the current scanning plane to generate the second plane image of the current scanning plane, other image processing methods achieving resolution enhancement for the first plane image of the current scanning plane can be adopted, which is not limited herein.

In the implementations of the method for MRI scanning disclosed, the process of generating the second plane image is demonstrated, and second plane image with a higher resolution is generated from a lower-resolution first plane image by using an appropriate imaging model, thereby effectively ensuring the imaging quality of MR scanning.

Corresponding to the various implementations of the method for MRI scanning presented above, the present disclosure further provides implementations of the apparatus for MRI scanning. Since the apparatus for MRI scanning disclosed in the present disclosure corresponds to the method for MRI scanning illustrated in the above, the implementation manners of the method for MRI scanning described above are also applicable to the apparatus for MRI scanning disclosed herein, and will not be described in detail in the following examples.

FIG. 15 illustrates the structural diagram of the apparatus for MRI scanning in one implementation of the disclosure. As shown in FIG. 15, the apparatus for MRI scanning 100 includes a generation module 11, a determination module 12, an acquisition module 13, and an imaging module 14.

The generation module 11 is configured to acquire original k-space data of a current scanning plane in the current scanning plane segment, and generate a first plane image of the current scanning plane based on the original k-space data.

The determination module 12 is configured to determine a type of the current scanning plane.

In some implementations, the determination module 12 is configured to determine whether the current scanning plane is of a first type, where the first type of scanning plane is imaged with an intra-frame imaging mode.

The acquisition module 13 is configured to determine a prediction mode of the current scanning plane based on the type of the current scanning plane.

In some implementations, the acquisition module 13 is configured to determine, in response to the current scanning plane being a non-first type of scanning plane or to the prediction mode is a MR inter-frame prediction mode, a neighboring scanning plane corresponding to the current scanning plane, and acquire a second plane image of the neighboring scanning plane, where a resolution of the second plane image is higher than that of the first plane image.

The imaging module 14 is configured to generate a second plane image of the current scanning plane by performing imaging prediction for the current scanning plane based on the first plane image of the current scanning plane.

In some implementations, the imaging module 14 is configured to generate, in response to the current scanning plane being of a non-first type or to the prediction mode is a MR inter-frame prediction mode, the second plane image of the current scanning plane based on the first plane image of the current scanning plane and the second plane image of the neighboring scanning plane.

Figures 16, 17:
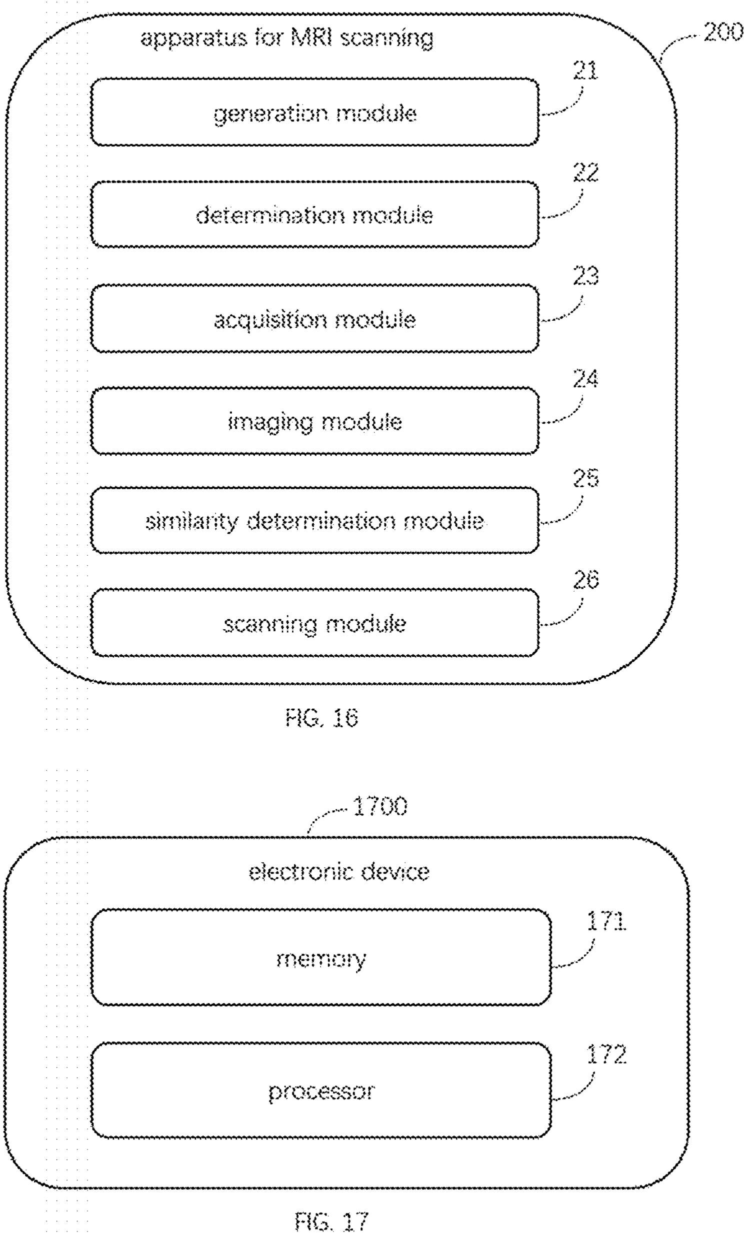
FIG. 16 is a schematic structural diagram illustrating the apparatus for MRI scanning in another implementation of the present disclosure.
FIG. 17 is a block diagram illustrating an electronic device in an implementation of the present disclosure.

FIG. 16 illustrates the structural diagram of the apparatus for MRI scanning in one implementation of the disclosure. As shown in FIG. 16, the apparatus for MRI scanning 200 includes a generation module 21, a determination module 22, an acquisition module 23, an imaging module 24, a similarity determination module 25, and a scanning module 26.

The generation module 21, the determination module 22, the acquisition module 23, and the imaging module 24 may have the same structures and functions as the generation module 11, the determination module 12, the acquisition module 13, and the imaging module 14, respectively.

In some implementations of the present disclosure, the imaging module 24 is further configured to: in the case where the current scanning plane is the first type of scanning plane, performing intra-frame imaging for the current scanning plane based on the first plane image to generate the second plane image of the current scanning plane.

In some implementations, the apparatus for MRI scanning 200 further includes a similarity determination module 25.

The similarity determination module 25 is configured to obtain, in response to the current scanning plane being of the non-first type, a structural similarity between the first plane image of the current scanning plane and at least one of a first plane image or a second plane image of the neighboring scanning plane. The imaging module 24 is configured to generate, in response to the structural similarity being greater than a predetermined similarity threshold, the second plane image of the current scanning plane based on the first plane image of the current scanning plane and the second plane image of the neighboring scanning plane.

In some implementations of the present disclosure, the similarity determination module 25 is further configured to move, in the case where the structural similarity is less than or equal to the predetermined similarity threshold, the current scanning plane to the next scanning plane segment.

In some implementations, the similarity determination module 25 is further configured to save at least one of the k-space data or the first plane image of the current scanning plane in the case where the structural similarity is less than or equal to the predetermined similarity threshold.

In some implementations, the generation module 21 is further configured to use the saved first plane image as the first plane image of the current scanning plane in the case where the scanning reaches the scanning position of the current scanning plane in the next scanning plane segment, and where the current scanning plane after the movement is not of the first type in the next scanning plane segment. Alternatively, the generation module 21 is further configured to perform, in the case that the current scanning plane after the movement is of the first type of scanning plane in the next scanning plane segment, supplemental acquisition of the original k-space data of the current scanning plane based on a sampling rate of the first type of scanning plane, and re-generate the first plane image of the current scanning plane based on the k-space data obtained after the supplemental acquisition.

In some implementations, the acquisition module 23 is further configured to obtain the prediction mode of the current scanning plane, where the MR inter-frame prediction mode includes unidirectional inter-frame prediction or bi-directional inter-frame prediction, and determine, based on the prediction mode, a preceding scanning plane of the first type or the second type as a neighboring scanning plane corresponding to the current scanning plane.

In some implementations, the acquisition module 23 is further configured to determine, in the case where the prediction mode is the unidirectional inter-frame prediction, a forward predicted scanning plane on which prediction of the current plane image depends as the neighboring scanning plane. The acquisition module 23 is further configured to determine, in the case where the prediction mode is the bidirectional inter-frame prediction, both a forward predicted scanning plane and a backward predicted scanning plane on which predication of the current plane image as the neighboring scanning plane corresponding to the current scanning plane.

In some implementations, the apparatus for MRI scanning 200 further includes a scanning module 26.

The scanning module 26 is configured to perform, in the case where the current scanning plane is a plane set including multiple sub-scanning planes, inter-frame prediction for each sub-scanning plane in the plane set by starting from the initial sub-scanning plane of the plane set, and to generate a second plane image corresponding to each sub-scanning plane in the plane set, until imaging of all the sub-scanning planes in the plane set is completed, and to proceed to the next scanning plane or the next scanning plane segment.

In some implementations, the imaging module 24 is further configured to perform feature extraction on the input plane image by a feature extraction layer and output a feature image, where the input plane image is the first plane image of the current scanning plane and the second plane image of the neighboring scanning plane in case of the MR inter-frame prediction, and the input plane image is the first plane image of the current scanning plane in case of the MR intra-frame imaging. The imaging module 24 is further configured to generate predicted k-space data by a data processing layer based on the feature image, generate a predicted enhanced plane image of the current scanning plane based on the predicted k-space data, input the predicted enhanced plane image into an image enhancement layer, output residual information, and generate the second plane image of the current scanning plane based on the residual information and the predicted enhanced plane image.

In some implementations, the imaging module 24 is configured to replace the predicted data at the same position in the predicted k-space data as the original k-space data to generate target k-space data, and generate a predicted enhancement plane image of the current layer based on the target k-space data.

In some implementations, the imaging module 24 is configured to perform MR intra-frame imaging by an MR intra-frame imaging model, or to perform MR inter-frame prediction by an MR inter-frame prediction model. Both the MR inter-frame prediction model and the MR intra-frame imaging model include multiple image processing units connected in sequence. Each image processing unit includes a feature extraction layer, a data processing layer, and an image enhancement layer. The feature extraction layer, the data processing layer, and the image enhancement layer in each image processing unit are connected in sequence, and the output of the image enhancement layer is an input of the feature extraction layer of the next image processing unit.

The apparatus for MRI scanning provided in the implementations of the present disclosure obtains the original k-space data of the current scanning plane in the current scanning plane segment, generates the first plane image corresponding to the current scanning plane, and then determines the type of the current scanning plane. Subsequently, the second plane image of the current scanning plane is generated based on the first plane image of the current scanning plane with the prediction mode corresponding to the type of the current scanning plane. In the implementations of the present disclosure, a low-resolution first plane image corresponding to each scanning plane is first obtained, and a high-resolution second plane image is then obtained by resolution processing on the first plane image, which effectively shortens the imaging time. By utilizing the structural correlation between neighboring plane images, the second plane image corresponding to each scanning plane can be generated by prediction, which effectively reduces the scanning time. Different scanning planes in each scanning plane segment are separately scanned and imaged, ensuring image quality, and achieving the goal of high-speed, high-quality MRI scanning and imaging.

In order to implement the implementations described above, and to achieve the objectives of the implementations, the present disclosure also proposes an electronic device, a computer-readable storage medium, a computer program product, and a computer program.

In some implementations, the electronic device is an MRI device.

FIG. 17 shows a schematic diagram of an example electronic device 1700 applicable to implement the implementations disclosed herein. The electronic device 1700 includes a memory 171 and a processor 172. The processor 172 runs a program corresponding to executable program code by reading the executable program code stored in the memory 171, so as to implement the method for MRI scanning described above. The memory 171 may be communicatively connected to the processor 172.

In the electronic device in some implementations, by executing, by the processor 172, a computer program stored in the memory 171, the original k-space data of the current scanning plane in each scanning plane segment is obtained, the first plane image corresponding to the current scanning plane is generated, and the type of the current scanning plane is determined. After determining the type of the current scanning plane, the second plane image of the current scanning plane is generated based on the first plane image of the current scanning plane with a prediction mode corresponding to the type of the current scanning plane.

In some implementations, in response to the current scanning plane being of a non-first type, a second plane image of a neighboring scanning plane corresponding to the current scanning plane is obtained, and the second plane image corresponding to the current scanning plane is generated based on the first plane image of the current scanning plane and the second plane image corresponding to the neighboring scanning plane.

In the implementations of the present disclosure, a low-resolution first plane image corresponding to each scanning plane is first obtained, and a high-resolution second plane image is then obtained by resolution processing on the first plane image, which effectively shortens the imaging time. The second plane image corresponding to each scanning plane can be generated by prediction, which effectively reduces the scanning time. Different scanning planes in each scanning plane segment are separately scanned and imaged, ensuring image quality, and achieving the goal of high-speed, high-quality MRI scanning and imaging.

The present disclosure further provides a computer-readable storage medium storing a computer program that, when executed by a processor, implements the method for MRI scanning as described above.

In the computer-readable storage medium in the implementations, by storing a computer program and executing the computer program by a processor, the original k-space data of the current scanning plane in each scanning plane segment is obtained, the first plane image corresponding to the current scanning plane is generated, and the type of the current scanning plane is determined. After determining the type of the current scanning plane, the second plane image of the current scanning plane is generated based on the first plane image of the current scanning plane with a prediction mode corresponding to the type of the current scanning plane.

In the implementations of the present disclosure, a low-resolution first plane image corresponding to each scanning plane is first obtained, and a high-resolution second plane image is then obtained by resolution processing on the first plane image, which effectively shortens the imaging time. The second plane image corresponding to each scanning plane can be generated by prediction, which effectively reduces the scanning time. Different scanning planes in each scanning plane segment are separately scanned and imaged, ensuring image quality, and achieving the goal of high-speed, high-quality MRI scanning and imaging.

The present disclosure further provides a computer program product that includes a computer program. The computer program product, when executed by a processor, implements the method for MRI scanning described above.

The computer program product in the implementations includes a computer program. In response to the execution of the computer program by a processor, the original k-space data of the current scanning plane in each scanning plane segment is obtained, the first plane image corresponding to the current scanning plane is generated, and the type of the current scanning plane is determined. After determining the type of the current scanning plane, the second plane image of the current scanning plane is generated based on the first plane image of the current scanning plane with a prediction mode corresponding to the type of the current scanning plane.

In the implementations of the present disclosure, a low-resolution first plane image corresponding to each scanning plane is first obtained, and a high-resolution second plane image is then obtained by resolution processing on the first plane image, which effectively shortens the imaging time. The second plane image corresponding to each scanning plane can be generated by prediction, which effectively reduces the scanning time. Different scanning planes in each scanning plane segment are separately scanned and imaged, ensuring image quality, and achieving the goal of high-speed, high-quality MRI scanning and imaging.

The present disclosure further provides a computer program including computer program codes. Execution of the computer program codes on a computer causes the computer to execute the method for MRI scanning as described above.

In the computer program in the implementations, by executing the computer program code stored therein by the computer, the original k-space data of the current scanning plane in each scanning plane segment is obtained, the first plane image corresponding to the current scanning plane is generated, and the type of the current scanning plane is determined. After determining the type of the current scanning plane, the second plane image of the current scanning plane is generated based on the first plane image of the current scanning plane with a prediction mode corresponding to the type of the current scanning plane.

In the implementations of the present disclosure, a low-resolution first plane image corresponding to each scanning plane is first obtained, and a high-resolution second plane image is then obtained by resolution processing on the first plane image, which effectively shortens the imaging time. The second plane image corresponding to each scanning plane can be generated by prediction, which effectively reduces the scanning time. Different scanning planes in each scanning plane segment are separately scanned and imaged, ensuring image quality, and achieving the goal of high-speed, high-quality MRI scanning and imaging.

It should be noted that the explanations and descriptions in the above implementations of the method for MRI scanning are also applicable to the computer device, computer-readable storage medium (such as non-transitory computer-readable storage medium storing computer instructions), the computer program product, or the computer program (such as computer instructions) described in the above implementations, which are not repeated herein.

It should be understood that, in the description of the present disclosure, directions or positional relationships indicated by terms such as "center", "longitudinal", "lateral", "length", "width", "thickness", "top", "bottom", "front", "rear", "left", "right", "vertical", "horizontal", "top", "bottom", "inner", "outer", "clockwise", "counter-clockwise", "axial", "radial", "circumferential" or the like, are based on the orientations or positional relationships shown in the accompanying drawings. The terms are intended only to facilitate the description of the present disclosure and to simplify the description, and are not intended to indicate or imply that the device or element referred to must have a specific orientation, be constructed or operated in a specific orientation, and should not be understood as limiting the present disclosure.

Furthermore, terms such as "first" and "second" are used for descriptive purposes only and are not to be understood as indicating or implying relative importance or indicating the number of technical features indicated. Thus, a feature limited by the term "first" or "second" can explicitly or implicitly include one or more such features. In the description of the present disclosure, the term "multiple" means two or more unless otherwise specifically defined.

In the present disclosure, unless otherwise explicitly specified and limited, terms such as "mounted", "connected", "coupled", "fixed", etc., should be broadly interpreted, such as, for example, interpreted as either fixedly connected, detachably connected, or integrally connected. It can be mechanically connected or electrically connected. It can be directly connected or indirectly connected through intermediate media. It can be inside one element or inside multiple elements and interact with each other. For those of ordinary skill in the art, the specific meaning of the terms in the present disclosure can be understood on a case-by-case basis.

In the present disclosure, unless otherwise explicitly specified and limited, the first feature being "on" or "below" the second feature can be a direct contact between the first and second features, or an indirect contact between the first and second features through an intermediate medium. Moreover, the first feature being "above", "upward", or "on top of" the second feature can be that the first feature is directly above or inclined above the second feature, or it merely mean that the first feature is horizontally higher than the second feature. The first feature being "below", "downward", and "underneath" the second feature can be that the first feature is directly below or inclined below the second feature, or it merely means that the first feature is horizontally lower than the second feature.

In the description of this disclosure, reference terms such as "one implementation", "some implementations", "an example", "specific examples", or "some examples", etc., are used for descriptive purposes and indicate that specific features, structures, materials, or characteristics described in conjunction with the implementations or examples are included in at least one implementation or at least one example of the present disclosure. In the description of this disclosure, schematic expressions of the above terms are not necessarily directed to the same implementations or examples, and the specific features, structures, materials, or characteristics described can be combined in any one or more implementations or examples in a suitable manner. Moreover, those skilled in the art can combine different implementations or examples and the features thereof described in this specification in a suitable manner without contradicting each other.

Although implementations of the present disclosure have been described and illustrated in detail, it can be understood that the above implementations are just examples and should not be construed as limiting the disclosure. Those of ordinary skill in the art can make changes, modifications, substitutions, and variations to the above implementations.

What is claimed is:

1. A method for magnetic resonance imaging (MRI) scanning, comprising:

acquiring original k-space data of a current scanning plane in a current scanning plane segment, and generating a first plane image of the current scanning plane based on the original k-space data;

determining a type of the current scanning plane based on an under-sampling factor of the current scanning plane;

determining a prediction mode for the current scanning plane based on the type of the current scanning plane, wherein the prediction mode comprises a MR intra-frame imaging mode or a MR inter-frame prediction mode; and generating a second plane image of the current scanning plane with the determined prediction mode based on the first plane image of the current scanning plane, wherein a resolution of the second plane image is greater than a resolution of the first plane image.

2. The method of claim 1, wherein generating the second plane image of the current scanning plane with the determined prediction mode based on the first plane image of the current scanning plane, comprises:

in response to the prediction mode for the current scanning plane being the MR inter-frame prediction mode, determining a neighboring scanning plane corresponding to the current scanning plane, and obtaining a second plane image of the neighboring scanning plane; and performing imaging prediction for the current scanning plane based on the first plane image of the current scanning plane and the second plane image of the neighboring scanning plane to generate the second plane image of the current scanning plane.

3. The method of claim 2, further comprising:

before performing the imaging prediction for the current scanning plane based on the first plane image of the current scanning plane and the second plane image of the neighboring scanning plane:

obtaining a structural similarity between the first plane image of the current scanning plane and at least one of a first plane image or the second plane image of the neighboring scanning plane; and performing the imaging prediction for the current scanning plane based on the first plane image of the current scanning plane and the second plane image of the neighboring scanning plane, further comprising:

in response to determining that the structural similarity is greater than a preset similarity threshold, performing the imaging prediction for the current scanning plane based on the first plane image of the current scanning plane and the second plane image of the neighboring scanning plane.

4. The method of claim 3, further comprising:

in response to the structural similarity being less than or equal to the preset similarity threshold, moving the current scanning plane to a next scanning plane segment, or in response to the structural similarity being less than or equal to the preset similarity threshold, saving at least one of the k-space data of the current scanning plane or the first plane image of the current scanning plane.

5. The method of claim 4, further comprising:

after moving the current scanning plane to the next scanning plane segment, in response to scanning of the next scanning plane segment proceeding to a scanning position of the current scanning plane, using a saved first plane image as the first plane image of the current scanning plane; or, performing supplementary acquisition of the original k-space data of the current scanning plane, and regenerating a first plane image of the current scanning plane based on the k-space data obtained after the supplementary acquisition.

6. The method of claim 2, wherein the MR inter-frame prediction mode comprises a unidirectional inter-frame prediction mode or a bidirectional inter-frame prediction mode, and determining the neighboring scanning plane corresponding to the current scanning plane further comprises:

in response to determining that the prediction mode is the unidirectional inter-frame prediction mode, determining a forward predicted neighboring scanning plane in the current scanning plane segment as the neighboring scanning plane corresponding to the current scanning plane; or in response to determining that the prediction mode is the bidirectional inter-frame prediction mode, determining both a forward predicted scanning plane and a backward predicted scanning plane in the current scanning plane segment as the neighboring scanning plane corresponding to the current scanning plane.

7. The method of claim 2, wherein determining the neighboring scanning plane corresponding to the current scanning plane further comprises:

determining a preceding scanning plane of the first type or the second type corresponding to a scanning position near to that of the current scanning plane as the neighboring scanning plane corresponding to the current scanning plane.

8. The method of claim 2, further comprising:

in response to determining that the current scanning plane is a plane set comprising a plurality of sub-scanning planes, performing, by starting from an initial sub-scanning plane of the plane set, MR inter-frame prediction for each sub-scanning plane in the plane set, and generating a second plane image for each sub-scanning plane in the plane set, until imaging of all the sub-scanning planes in the plane set is completed, and then proceeding to a next scanning plane or a next scanning plane segment.

9. The method of claim 1, wherein generating the second plane image of the current scanning plane with the determined prediction mode based on the first plane image of the current scanning plane, comprises:

in response to the prediction mode for the current scanning plane being the MR intra-frame imaging mode, performing intra-frame imaging based on the first plane image of the current scanning plane to generate the second plane image of the current scanning plane.

10. The method of claim 1, wherein the type of the current scanning plane comprises a first type or a non-first type, the first type of scanning plane corresponding to a first under-sampling factor smaller than an under-sampling factor corresponding to the non-first type of scanning plane; and wherein determining the prediction mode for the current scanning plane based on the type of the current scanning plane, comprises:

in response to the current scanning plane being of the first type, determining the MR intra-frame imaging mode as the prediction mode for the current scanning plane; and in response to the current scanning plane being of the non-first type, determining the MR inter-frame prediction mode as the prediction mode for the current scanning plane.

11. The method of claim 1, wherein the type of the current scanning plane comprises a first type, a second type or a third type, each corresponding to an under-sampling factor different from each other, the MR inter-frame prediction mode comprising a unidirectional inter-frame prediction mode and a bidirectional inter-frame mode; and wherein determining the prediction mode for the current scanning plane based on the type of the current scanning plane comprises:

in response to the current scanning plane being of the second type, determining the unidirectional inter-frame prediction mode as the prediction mode for the current scanning plane; and in response to the current scanning plane being of the third type, determining the bidirectional inter-frame prediction mode as the prediction mode for the current scanning plane.

12. The method of claim 1, wherein generating the second plane image of the current scanning plane comprises:

performing feature extraction on an input plane image to obtain a feature image, wherein the input plane image comprises the first plane image of the current scanning plane;

generating predicted k-space data for the feature image, and generating a predicted enhancement plane image of the current scanning plane based on the predicted k-space data;

obtaining residual information of the predicted enhancement plane image; and generating the second plane image of the current scanning plane based on the residual information and the predicted enhancement plane image.

13. The method of claim 12, wherein generating the predicted enhancement plane image of the current scanning plane based on the predicted k-space data comprises:

replacing the predicted k-space data on a position same as that in the original k-space data with the original k-space data to generate target k-space data; and generating the predicted enhancement plane image of the current scanning plane based on the target k-space data.

14. The method of claim 12, wherein in the MR intra-frame imaging mode, an MR intra-frame imaging model is utilized, and in the MR inter-frame prediction mode, an MR inter-frame prediction model is utilized, the MR inter-frame prediction model and the MR intra-frame imaging model both comprising multiple image processing units connected in sequence, each image processing unit comprising a feature extraction layer, a data processing layer, and an image enhancement layer connected in sequence, and an output of the image enhancement layer in an image processing unit being taken as an input of the feature extraction layer of a next image processing unit; or wherein the input plane image further comprises a second plane image of a neighboring scanning plane in a case of the prediction mode being the MR inter-frame prediction mode.

15. The method of claim 1, wherein the current scanning plane segment comprises a plurality of scanning planes, and the plurality of scanning planes are scanned by under-sampling with different under-sampling factors.

16. A non-transitory computer-readable storage medium storing computer instructions, wherein:

the computer instructions are configured to cause a computer to execute the method of claim 1.

17. A computer program product comprising a computer program, wherein:

the computer program, when executed by a processor, implements the method of claim 1.

18. An electronic device for magnetic resonance imaging (MRI) scanning, comprising:

at least one processor; and a memory communicatively connected to the at least one processor;

wherein the memory stores instructions executable by the at least one processor, and execution of the instructions by the at least one processor causes the at least one processor to:

acquire original k-space data of a current scanning plane in a current scanning plane segment, and generating a first plane image of the current scanning plane based on the original k-space data;

determine a type of the current scanning plane based on an under-sampling factor of the current scanning plane;

determine a prediction mode for the current scanning plane based on the type of the current scanning plane, wherein the prediction mode comprises a MR intra-frame imaging mode or a MR inter-frame prediction mode; and generate a second plane image of the current scanning plane with the determined prediction mode based on the first plane image of the current scanning plane, wherein a resolution of the second plane image is greater than a resolution of the first plane image.

19. The electronic device of claim 18, wherein generating the second plane image of the current scanning plane with the determined prediction mode based on the first plane image of the current scanning plane, comprises:

in response to the prediction mode for the current scanning plane being the MR inter-frame prediction mode, determining a neighboring scanning plane corresponding to the current scanning plane, and obtaining a second plane image of the neighboring scanning plane; and performing imaging prediction for the current scanning plane based on the first plane image of the current scanning plane and the second plane image of the neighboring scanning plane to generate the second plane image of the current scanning plane.

20. The electronic device of claim 18, wherein the type of the current scanning plane comprises a first type or a non-first type, the first type of scanning plane corresponding to a first under-sampling factor smaller than an under-sampling factor corresponding to the non-first type of scanning plane; and wherein determining the prediction mode for the current scanning plane based on the type of the current scanning plane, comprises:

in response to the current scanning plane being of the first type, determining the MR intra-frame imaging mode as the prediction mode for the current scanning plane; and in response to the current scanning plane being of the non-first type, determining the MR inter-frame prediction mode as the prediction mode for the current scanning plane.

* * * * *